(12) United States Patent
Ahmed et al.

(10) Patent No.: US 10,813,882 B1
(45) Date of Patent: Oct. 27, 2020

(54) IN SITU GELLING FORMULATION FOR REDUCED INITIAL DRUG BURST

(71) Applicant: King Abdulaziz University, Jeddah (SA)

(72) Inventors: Tarek A. Ahmed, Jeddah (SA); Mohammed M. Mussari, Jeddah (SA); Abdelsattar M. Omar, Jeddah (SA); Khalid M. El-Say, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 16/705,407

(22) Filed: Dec. 6, 2019

Related U.S. Application Data

(60) Provisional application No. 62/939,777, filed on Nov. 25, 2019.

(51) Int. Cl.

| | |
|---|---|
| *A61K 9/06* | (2006.01) |
| *A61K 47/34* | (2017.01) |
| *A61K 9/00* | (2006.01) |
| *A61K 47/10* | (2017.01) |
| *A61K 31/505* | (2006.01) |
| *A61K 47/26* | (2006.01) |

(52) U.S. Cl.
CPC .............. *A61K 9/06* (2013.01); *A61K 9/0019* (2013.01); *A61K 31/505* (2013.01); *A61K 47/10* (2013.01); *A61K 47/26* (2013.01); *A61K 47/34* (2013.01)

(58) Field of Classification Search
CPC .................................. A61K 9/0019; A61K 9/06
See application file for complete search history.

(56) References Cited

U.S. PATENT DOCUMENTS 8,940,311 B2    1/2015  Lim et al.

9,597,402 B2 *  3/2017  Luk .............. A61K 31/519
2014/0348810 A1  11/2014  Shalaby

OTHER PUBLICATIONS

Varzakas, T. et al., "Mixing emulsions", Food Engineering Handbook, 2015, CRC Press, p. 222.*
Clearfield, M. et al., "Comparison of the efficacy and safety of rosuvastatin 10 mg and atorvastatin 20 mg in high-risk pateints with hypercholesterolemia", Trials, 7:35, printed from https://trialsjournal.biomedcentral.com/track/pdf/10.1186/1745-6215-7-35.*
Ahmed, T. et al. "Preparation of parenteral in situ gel formulations based on smart PLGA polymers: concepts to decrease initial drug burst and extend the drug release", Biodegradable Polymers: Recent developments and new perspectives, 2017, IAPC Publishing, Chapter 9.*
Lo, J. et al. "Nonionic microemulsions as solubilizers of hydrophobic drugs: solubilization of paclitaxel", Materials, 2016, 9, 761.*
Cremophor Grades, Technical Information, Jun. 2006, BASF.*
Ahmed et al., "Depot injectable atorvastatin biodegradable in situ gel: development, optimization, in vitro, and in vivo evaluation" Drug Design, Development and Therapy, Jan. 20, 2016:10 405-415.
Gurram et al., "Role of Components in the Formation of Self-microemulsifying Drug Delivery Systems", Indian J Pharm Sci. May-Jun. 2015; 77(3): 249-257.
Park et al., "Controlled Release of Simvastatin from In situ Forming Hydrogel Triggers Bone Formation in MC3T3-E1 Cells", The AAPS Journal, vol. 15, No. 2, Apr. 2013.
Pradeep et al., "Rosuvastatin 1.2 mg in Situ Gel Combined With 1:1 Mixture of Autologous Platelet-Rich Fibrin and Porous Hydroxyapatite Bone Graft in Surgical Treatment of Mandibula Class II Furcation Defects: A Randomized Clinical Control Trial", Journal of Periodontology, vol. 87, Issue 1, Jan. 1, 2016.

* cited by examiner

*Primary Examiner* — Gina C Justice
(74) *Attorney, Agent, or Firm* — W & C IP

(57) ABSTRACT

An in situ gel formulation comprising poly lactide-co-ε-caprolactone (PLCL), a surfactant with a hydrophilic-lipophilic balance value of 14-15, a plasticizer, and a statin is provided. Methods of treating hyperlipidemia by parenterally administering the in situ gel formulation are also provided.

3 Claims, 7 Drawing Sheets

IN SITU GELLING FORMULATION FOR REDUCED INITIAL DRUG BURST

CROSS-REFERENCE TO RELATED APPLICATIONS

This application claims the benefit of U.S. Provisional Application 62/939,777 filed Nov. 25, 2019, the complete contents of which are incorporated herein by reference.

FIELD OF THE INVENTION

The invention is generally related to an in situ gelling composition that lowers the initial drug burst and effectively reduces hyperlipidemia.

BACKGROUND OF THE INVENTION

In situ gel (ISG) systems are formulations that exist in the liquid state, but are transformed into a gel once in contact with the biological environment of the body, allowing the drug to be released in a sustained/controlled manner. The process of in situ gelation can be triggered by multiple factors such as pH change, temperature change, availability of ions, UV radiation, and others.[1] The main drawback of these systems is the accompanied initial drug release (burst effect) which may cause severe toxicity and tissue irritation.[2,3] Initial drug burst effect is attributed to escape of the drug to the surrounding tissue before complete hardening of the polymer, and also due to uneven distribution of the drug within the polymeric matrix.[4-6] ISG systems depend on the presence of smart polymers which are macromolecules that demonstrate a dramatic change in response to a certain stimulus such as temperature, pH, magnetic field, light, or solvent exchange. Smart polymers have been utilized in pharmaceutical formulations of many drug delivery systems due to their biodegradability, biocompatibility, ease of application, site specific drug delivery actions and extended release mechanisms. These polymers may be either natural or synthetic.[7,8]

Initial drug burst is the major drawback of ISG systems. In this phenomenon, a high amount of the drug loaded is released during the early release phase, in the first 24 h, that may result in a plasma toxic drug level. This is mainly caused by the presence of lag time between the ISG administration and complete solidification.[14,15] Other possible causes for this behavior are attributed to the amount of drug adsorbed on the ISG surface and the unequal drug distribution in the polymeric matrix which may cause rapid and high initial drug diffusion into the release medium.[5,6]

Thus, new ISG formulations are needed to improve drug efficacy and achieve a sustained release drug action.

SUMMARY OF THE INVENTION

An aspect of the disclosure provides an in situ gel formulation comprising poly lactide-co-ε-caprolactone (PLCL), a surfactant with a hydrophilic-lipophilic balance value of 14-15, a plasticizer, and a statin. In some embodiments, the statin is rosuvastatin. In some embodiments, the ratio of lactide to caprolactone in PLCL is 25:75. In some embodiments, the PLCL concentration is 40-45% w/v. In some embodiments, the surfactant is sorbitan monopalmitate 40 or polysorbate 80. In some embodiments, the plasticizer is polyethylene glycol (PEG) 400. In some embodiments, the ratio of surfactant: PEG 400 is 80:20.

Another aspect of the disclosure provides a method of treating hyperlipidemia in a subject in need thereof, comprising parenterally administering an in situ gel formulation as described herein. In some embodiments, release of the statin from the in situ gel formulation does not exceed 15% within 24 hours of administration. In some embodiments, the in situ gel formulation provides sustained release of the statin for at least 21 days.

DETAILED DESCRIPTION

Figure 1A:
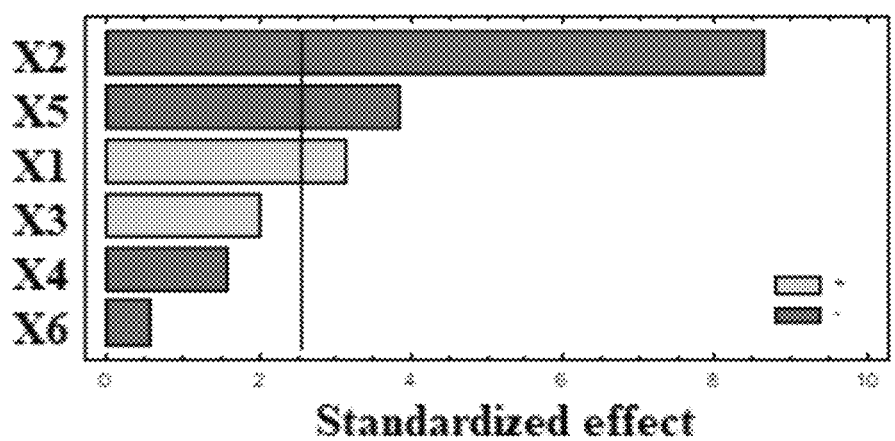
FIG. 1A-C. Standardized Pareto charts for the effect of the independent variables on (A) $Y_1$, (B) $Y_2$, and (C) $Y_3$ for the Plackett-Burman design ISG formulations. Abbreviations: $X_1$, Poly lactide-co-ε-caprolactone concentration; $X_2$, polylactide to polycaprolactone ratio; $X_3$, molecular weight of polyethylene glycol; $X_4$, polyethylene glycol concentration; $X_5$, surfactant Hydrophilic-Lipophilic Balance; $X_6$, surfactant concentration; $Y_1$, rosuvastatin release after 0.5 h; $Y_2$, rosuvastatin release after 2 h; $Y_3$, rosuvastatin release after 24 h.

Embodiments of the disclosure provide in situ gelling formulations that lower the initial drug burst and achieve a sustained release drug action useful for the parenteral delivery of biological active agents such as statins. The formulations described herein are an alternative to currently available marketed oral tablet products.

The polymeric matrix forming the in situ gelling system may be comprised of poly lactide-co-ε-caprolactone (PLCL), a copolymer made of L-lactide and ε-caprolactone which has been approved by the united states food and drug administration (FDA).[10] PLCL is a flexible, elastic, durable and biodegradable polymer. The elasticity of this polymer is provided by the caprolactone moiety and the toughness by the lactide moiety. PLCL is degraded in the body into lactic acid and caproic acid which are then metabolized by the tricarboxylic acid cycle and execrated through the kidney.[13]

The characteristics of PLCL are dependent on the molecular weight and the ratio of both lactic and caprolactone in the polymer chain. PLCL with a higher poly-caprolactone ratio results in a more hydrophobic polymer.[36] In some embodiments, the PLCL has a lactide to caprolactone ratio of about 25:75 to about 80:20. In some embodiments, the PLCL concentration is 20-60% w/v, e.g. 30-50%, e.g. 40-45% in a solvent such as N-methyl-2-pyrrolidone. Other suitable solvents include, but are not limited to dimethylsulphoxide, triacetin and 2-pyrrolidone. It should be understood that throughout the specification the term weight percent (wt %) refers to mass per unit volume, unless otherwise specified.

The in situ gelling formulation may also include one or more surfactants, e.g. polysorbates, sorbitan esters of fatty acids, cetearyl glucoside or poloxamers or other stabilisers such as xanthan gum, or propylene glycol alginate. In some embodiments, the surfactant is one or more of sorbitan monopalmitate 20, sorbitan monopalmitate 40, sorbitan monopalmitate 80, polysorbate 20, polysorbate 60, polysorbate 80, or polyoxyl castor oils such as PEG-35 castor oil and PEG-40 castor oil. In some embodiments, the total amount of surfactants in the compositions of the presently disclosed embodiments is about 1-15% of the total composition, e.g. 1-10% or 1-5%.

Surfactants are chemicals that are amphipathic, which means that they contain both hydrophobic and hydrophilic groups. The hydrophilic-lipophilic balance (HLB) of a surfactant is measured on an empirical scale developed by Griffin (W. C. Griffin, J. Cosmet. Chem., 1, 311, 1949). This scale ranges from 0 to 20, with 0 for a completely lipophilic molecule and 20 for a completely hydrophilic molecule. In some embodiments, the surfactant has a HLB value of about 11-17, e.g. 12-16, e.g. 14-15.

In some embodiments, the in situ gelling formulation includes a plasticizer to decrease the attraction force between polymer chains and so make them more flexible. Exemplary plasticizers include polyethylene glycol of varying molecular weights, e.g. from 300 g/mol to 10,000 g/mol. In some embodiments, the plasticizer is PEG 400. In some embodiments, the total amount of plasticizer in the compositions of the presently disclosed embodiments is about 1-15% of the total composition, e.g. 5-15% or 10-15%.

In some embodiments, the ratio of surfactant to plasticizer is from 70:30 to 90:10, e.g. 80:20.

The in situ gelling formulations described herein are useful for delivery of biologically active agents to a human or non-human animal subject. In some embodiments, the active agent has a solubility in water (w/v) which is 3% or less, e.g. 1% or less. In some embodiments, the active agent is statin, such as rosuvastatin, atorvastatin, fluvastatin, lovastatin, pitavastatin, pravastatin, and simvastatin. Statins are a class of lipid lowering agents that reduce cardiovascular disease in those people at high risk. They reduce the cholesterol level in the body by inhibiting the enzyme 3-hydroxy-3-methyl-glutaryl-coenzyme A (HMG-CoA) reductase which plays a key role in production of cholesterol. Suppression of this enzyme leads to reduction of atherosclerosis probability and the accompanied cardiovascular events. Statins have been investigated for their effectiveness in management of many diseases such as Parkinson's, Alzheimer's, irritable bowel syndrome, sclerosis, stroke, and chronic obstructive pulmonary diseases.[21] HMG-CoA reductase inhibitors are generally classified into hydrophilic and lipophilic inhibitors. The former tends to be distributed to the hepatic and extrahepatic tissues, whereas the latter group is more hepato-selective.[21] Poor bioavailability is a general criteria of the statin members due to their low water solubility, low permeability, high molecular weight and extensive first pass metabolism. Statins are mainly formulated as oral dosage form despite being poorly available after oral intake.

Rosuvastatin (RSV) is a member of this class that is mainly distributed to liver cells with low peripheral tissue distribution. The bioavailability of RSV is 20% and it is 88% bound to plasma protein with 19 h half-life. The drug is poorly soluble in water (0.0886 mg/mL), marginally soluble in ethanol and soluble in organic solvent such as DMSO, and dimethyl formamide (DMF).[22] RSV reaches the maximum plasma level after 3 to 5 hours, and the drug plasma level is proportional to the amount of RSV administered. Food does not affect the amount of RSV absorbed.[23]

Embodiments of the disclosure provide a long acting parenteral ISG formulation with minimum initial drug burst. In some embodiments, release of the active agent from the in situ gel formulation does not exceed 25%, e.g. 20% or 15%, within 24 hours of administration. In some embodiments, the in situ gel formulation provides sustained release of the statin for at least 21 days, e.g. for 34 days or more. Thus, the ISG formulation improves drug efficacy and achieves a sustained release drug action.

The in situ gelling compositions of the disclosure are suitable for parenternal administration, e.g. as an intramuscular injection. There are various changes in conditions that can trigger the gelling of an in situ gelling composition. Among these are changes in pH, osmolality, temperature, water concentration, and alterations in specific ion concentrations.

Temperature-sensitive in situ gelling compositions generally change from a sol to a gel when the temperature exceeds a critical solution temperature, which in the case of drug delivery systems must be reasonably close to body temperature. In some embodiments, the sol-gel transition temperature of the composition of the disclosure is at least 25° C., e.g. 25-35° C., e.g. 28-32° C., e.g. about 30° C.

The present disclosure also provides a method of treatment of a human or non-human animal subject by delivery of a substantially insoluble or sparingly soluble biologically active agent, said method comprising administering to said subject an in situ gelling composition of the invention as herein before defined.

The compositions of the present disclosure may also contain other components such as, but not limited to, antioxidants, additives, adjuvants, buffers, tonicity agents, bioadhesive polymers, and preservatives. In any of the compositions of this disclosure, the mixtures are preferably formulated at about pH 5 to about pH 8. This pH range may be achieved by the addition of buffers to the composition. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure also provide methods of preparing in situ gelling systems. Such methods are known in the art.

The compositions of the disclosure may be useful for the treatment of any disease or disorder that the included active agent is useful for treating. For example, if a statin is used, the composition or dosage form may be useful for the treatment of hyperlipidemia, e.g. to reduce triglycerides and/or cholesterol levels. The drug may thus be useful for the prevention of cardiovascular disease or decreasing mortality in those with pre-existing cardiovascular disease. Additional diseases that may be treated with the formulations described herein include Parkinson's, Alzheimer's, irritable bowel syndrome, sclerosis, stroke, and chronic obstructive pulmonary diseases.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. statin) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Injectable in situ gel (ISG) systems suffer from high initial drug release that may result in toxic effects. This work aimed to develop an injectable sustained release rosuvastatin (RSV)

ISG formulation with minimum initial drug burst and improved hyperlipidemic efficacy. Six formulation factors, that affect RSV release after 0.5, 2 and 24 h, have been screened and the significant ones were optimized utilizing an experimental design tool. The optimum ISG formulation components were physico-chemically characterized. Kinetic treatment, dissolution efficiency and mean dissolution time were investigated for the developed ISG formulations. Pharmacodynamic effects of the optimized ISG formulation were studied and compared to ISG formulation loaded with free RSV and to a marketed oral drug product. The poly lactide-co-ε-caprolactone (25:75) concentration, surfactant hydrophilic lipophilic balance and surfactant: polyethylene glycol 400 ratio were significantly affecting RSV release during the first 24 h. Physicochemical characterization demonstrated complete dispersion of RSV in the polymeric matrix with slight changes in the drug crystalline structure. The optimized formulation demonstrated acceptable syringeability, good flow rate and was able to extend the in vitro drug release for 34 days. The ISG formulations complied with the Weibull-model. Pharmacodynamic study revealed sustained reduction in the lipid profile that lasted for 21 days with a marked decrease in the lipid level during the first 24 h from the ISG system loaded with free RSV. The optimized RSV ISG formulation could reduce dosing frequency and enhance hypolipidemic efficacy.

Materials and Methods

Materials

Poly lactide-co-ε-caprolactone (PLCL) of 25:75 and 80:20 ratios were purchased from DURETEC Cooperation (Cupertino, Calif., USA). N-methyl-2-pyrrolidone (NMP) was supplied from Acros organics (Fair Lawn, N.J., USA). Rosuvastatin calcium was a kind gift from the Saudi Arabian Japanese Pharmaceuticals Co. Ltd (SAJA) (Jeddah, KSA). Polyethylene glycol (PEG), Mw 400 and 4000 were purchased from Fischer Scientific (Bartlesville, Okla., USA). Potassium dihydrogen orthophosphate was purchased from BDH chemicals Ltd (Poole, England). Sodium hydroxide was supplied from VWR international Ltd (Poole, England). TWEEN® (polysorbate) 80 and SPAN® (Sorbitan monopalmitate) 40 were obtained from Sigma-Aldrich (St. Louis, Mo.). Blood lipid diagnostic kit was purchased from Crescent diagnostics (Jeddah, KSA). All above materials were of analytical grade and were used without further purification.

Methods

Preliminary study: This section aimed to investigate the initial RSV release from a polymeric drug in situ gel (ISG) system that contains PLCL (25:75) and (80:20) without surfactant and/or plasticizer. Six ISG formulations were prepared by adding 20, 30 and 40% w/v of PLCL to NMP. The calculated amounts of the polymer were placed into scintillation glass vials containing the specified volume of NMP. Vials were subjected to probe sonication, to dissolve the polymer in NMP, using Sonics VIBRA-CELL™, VCX 750; Sonics & Materials, Inc. (Newtown, Conn., USA) for 10 minutes at an amplitude of 60% under ice cooling to prevent polymer degradation. The prepared formulations were kept in a shaking water bath (Model 1031; GLF Corp; Burgwedel, Germany) for 24 h at 25° C. until clear solutions were obtained. Known weight of RSV powder was subsequently added to each vial to yield a concentration of 40 mg/mL. Finally, the prepared vials were kept under shaking until complete dissolving of RSV.[24]

A quantity of each formulation equivalent to 20 mg RSV was injected into 900 mL phosphate buffer of pH 7.4 in a USP dissolution tester apparatus II at a rotation speed of 100 rpm and a temperature of 37±0.5° C. The in vitro drug release was studied for 24 h. Samples of 2 mL were withdrawn at 0.5, 2, and 24 h, and replaced with equivalent volume of phosphate buffer after each withdrawal. The concentration of RSV in the collected samples was measured spectrophotometrically at 242 nm using (6705 UV/Vis spectrophotometer; JENWAY). The accuracy of the spectrophotometric method and its freedom from any possible interference by the formulation excipients were verified. Recovery testing of the drug concentration in a solutions of drug and the studied excipients was verified. The experiment was done in triplicate. During the in vitro test, the dissolution tester was covered with aluminum foil to protect RSV from being degraded by light.

Plackett-Burman Screening Design

Six formulation factors that may affect the initial RSV release after 0.5 h ($Y_1$), 2 h ($Y_2$) and 24 h ($Y_3$) were screened using STATGRAPHICS® Centurion XV software (Stat-Point Technologies Inc, Warrenton, Va., USA). PLCL concentration ($X_1$), polylactide to polycaprolactone ratio ($X_2$), molecular weight of PEG ($X_3$), PEG concentration ($X_4$), surfactant Hydrophilic-Lipophilic Balance (HLB) ($X_5$) and surfactant concentration ($X_6$) were studied as independent variables. Based on our previously published work and the literature review; 0.5, 2 and 24 h of drug release were selected as dependent variables to optimize the release of rosuvastatin from the prepared ISG formulations. The composition of the ISG formulations obtained from the Plackett-Burman (PB) screening design is depicted in Table 1.

TABLE 1

Composition of the prepared rosuvastatin in situ gel formulations generated by the Plackett-Burman screening design, and the observed and predicted values of $Y_1$-$Y_3$.

| | $X_1$ | $X_2$ | $X_3$ | $X_4$ | $X_5$ | $X_6$ | $Y_1$ (%) | | $Y_2$ (%) | | $Y_3$ (%) | |
|---|---|---|---|---|---|---|---|---|---|---|---|---|
| Run | (%) | (Ratio) | (Mwt) | (%) | (HLB) | (%) | Observed | Preducted | Observed | Preducted | Observed | Predicted |
| 1 | 40 | 25:75 | 4000 | 15 | 4.3 | 5 | 13.34 ± 1.62 | 16.33 | 22.94 ± 2.37 | 22.19 | 31.8 + 3.61 | 31.67 |
| 2 | 20 | 80:20 | 4000 | 15 | 4.3 | 5 | 79.62 ± 0.84 | 71.45 | 81.51 ± 0.22 | 78.83 | 96.54 ± 1.27 | 94.61 |
| 3 | 40 | 25:75 | 400 | 5 | 4.3 | 5 | 15.87 ± 2.59 | 14.25 | 19.08 ± 1.36 | 21.99 | 25.14 ± 1.61 | 29.61 |
| 4 | 40 | 80:20 | 400 | 15 | 4.3 | 1 | 18.36 ± 1.40 | 24.03 | 31.09 ± 2.24 | 31.07 | 41.48 ± 2.96 | 37.68 |
| 5 | 20 | 25:75 | 400 | 5 | 4.3 | 1 | 55.53 ± 1.77 | 57.36 | 72.24 ± 2.04 | 69.97 | 85.23 ± 2.31 | 81.17 |
| 6 | 40 | 80:20 | 400 | 15 | 15 | 1 | 11.73 ± 1.74 | 6.05 | 17.44 ± 1.92 | 17.46 | 23.8 ± 2.60 | 27.50 |
| 7 | 20 | 80:20 | 400 | 5 | 15 | 5 | 49.51 ± 1.04 | 51.39 | 66.28 ± 1.32 | 65.01 | 84.0 ± 2.16 | 82.49 |
| 8 | 40 | 25:75 | 4000 | 5 | 15 | 1 | 16.83 ± 1.38 | 8.45 | 24.86 ± 2.09 | 21.54 | 34.78 ± 2.63 | 32.42 |
| 9 | 20 | 25:75 | 400 | 15 | 15 | 5 | 31.35 ± 1.23 | 29.26 | 42.75 + 2.81 | 43.39 | 59.18 ± 3.14 | 60.26 |
| 10 | 20 | 80:20 | 4000 | 5 | 4.3 | 1 | 82.27 ± 0.98 | 81.56 | 88.98 ± 1.85 | 91.79 | 100 ± 2.26 | 105.44 |
| 11 | 40 | 80:20 | 4000 | 5 | 15 | 5 | 13.46 ± 1.12 | 20.47 | 29.04 ± 2.49 | 30.19 | 45.80 ± 3.67 | 43.81 |
| 12 | 20 | 25:75 | 4000 | 15 | 15 | 1 | 34.18 ± 0.71 | 41.45 | 53.77 ± 1.39 | 56.56 | 72.15 ± 1.94 | 73.13 |

Abbreviations: $X_1$, poly lactic acid-co-ε-caprolactone concentration; $X_2$, polylactide: polycaprolactone ratio; $X_3$, molecular weight of PEG; $X_4$, PEG concentration; $X_5$, surfactant Hydrophilic-Lipophilic Balance; $X_6$, surfactant concentration; $Y_1$, drug release after 0.5 h; $Y_2$, drug release after 2 h; $Y_3$, drug release after 24 h.

Preparation and In Vitro Release Characterization

The PB ISG formulations were prepared by adding the accurately weighed amount of the studied polymer to a scintillation glass vial containing the specified volume of NMP. The calculated weight of surfactant (TWEEN® (polysorbate) 80 and SPAN® (Sorbitan monopalmitate) 40) and PEG (400 or 4000) were subsequently added. Vials were subjected to probe sonication under ice cooling and vials were kept shaking in a shaking water bath (Model 1031; GLF Corp; Burgwedel, Germany) until clear solutions were obtained. RSV (40 mg/mL) was finally added to each vial and mixed until complete dissolving of the drug.

Each ISG formulation was subjected to in vitro release study utilizing the same dissolution conditions previously mentioned. Withdrawn samples were quantified for RSV content after 0.5, 2, and 24 h.

Plackett-Burman Design Statistical Analysis

The observed values for $Y_1$, $Y_2$, and $Y_3$, were statistically analyzed and a p-value <0.05 was considered significant. The significant factors that affected the initial RSV burst from the prepared ISG formulations were identified.

Box-Behnken Optimization Design

Three different independent variables that affect the release of RSV after 0.5 h ($Y_1$), 2 h ($Y_2$) and 24 h ($Y_3$) were optimized using STATGRAPHICS® Centurion XV software (StatPoint Technologies Inc, Warrenton, Va., USA). Box-Behnken design was implemented to study the effect of PLCL (25:75) concentration ($X_1'$), the surfactant HLB ($X_2'$), and the surfactant to PEG 400 ratio ($X_3'$). The studied levels for $X_1'$, $X_2'$ and $X_3'$ were 35-45%, 13-15 and 0-100%, respectively. The aim was to produce RSV ISG formulation with a minimum initial drug burst.

Preparation and In Vitro Release of the Box-Behnken ISG Formulations

Fifteen different ISG formulations were prepared and the in vitro drug release profile was conducted as described above. A concentration of 10% PEG-Surfactant mixture was added to each formulation.

Box-Behnken Statistical Analysis and Optimum Desirability

The observed values for $Y_1$, $Y_2$ and $Y_3$ were statistically analyzed at p-value <0.05 to indicate the correlation between the independent and dependent variables. The optimum desirability was estimated, and the optimized formulation that contains the optimum levels of $X_1'$, $X_2'$ and $X_3'$ was prepared, characterized for $Y_1$, $Y_2$ and $Y_3$ as described above. The residual values for the predicted and observed responses were calculated.

Characterization of the Optimized Formulation

A quantity of each ISG formulation equivalent to 20 mg RSV was added into phosphate buffer of pH 7.4 utilizing the same conditions described above. Aliquots were withdrawn for 34 days and the release profile was constructed by plotting the cumulative percent of drug released versus time.

The ability of the optimized RSV ISG formulation to successfully flow through a syringe needle, syringeability, was also estimated.[24,25] This character was evaluated by measuring the magnitude of the force required to push the formulation through the needle using universal syringe rig (Stable Micro Systems, Surrey, UK). The formulation flow rate (mL/Second) was estimated using an apparatus designed in our laboratory. Known volume of the formulation was withdrawn in a plastic syringe of 20 G needle and a specified weight, equivalent to the predetermined force, was applied to the syringe plunger. The color, clarity, and pH of this formulation was also examined.

Kinetic Treatment of the In Vitro Release Data

The data obtained for the in vitro release of RSV from the fifteen Box-Behnken ISG formulations and the optimized ISG formulation were fitted to different mathematical models to investigate the drug release kinetics and release mechanism. The models used were; Zero,[26] First,[26] Weibull,[27] Hixson-Crowell,[28] Higuchi,[29] Korsmeyer-Peppas,[30,31] and Baker-Lonsdale.[32] The highest value of the coefficient ($R^2$) was used to identify the goodness of fit and the appropriate release model. Equations used for the studied kinetic orders/models are:

| | |
|---|---|
| $Q_t = K_o \cdot t$ | (Zero-order) |
| $\ln Q_t = \ln Q_o + K_1 \cdot t$ | (First-order) |
| $Q_t = K_H \cdot t^{1/2}$ | (Higuchi-model) |
| $M_t/M_a = Kt^n$ | (Korsmeyer-Peppas equation) |
| $\log[-\ln(1 - Q_t/Q_a)] = \beta \cdot \log t - \log a$ | (Weibull-model) |
| $W_o^{1/3} - W_t^{1/3} = K_s \cdot t$ | (Hixson-Crowell model) |
| $3/2[1 - (1 - Q_t/Q_a)^{2/3}] - Q_t/Q_a = K_L \cdot t$ | (Baker-Lonsdale model) |

Where $Q_t$ is the amount of RSV released at time (t), $Q_o$ is the initial amount of RSV released (mostly equal zero), $K_0$ and $K_1$ are the zero-order and first-order release constants and $K_H$ is the Higuchi-diffusion rate constant. $Q_t/Q_a$ is the fraction of RSV released at time t. $M_t/M_a$ represents the fraction of RSV released at time t, K is a constant comprising the structural and geometric characteristics of the prepared ISG formulation, and n is the release exponent that depends on the drug release mechanism. The parameter a is the scale parameter, that defines the time scale of the process, while β is the shape parameter, respectively. $W_o$ and $W_t$ are the initial and remaining amount of drug in the ISG formulation, respectively. $K_s$ is a constant incorporating the surface-volume relation. $K_L$ is the release constant that corresponds to the slope.

Kinetic treatment for the fifteen Box-Behnken ISG formulations was considered up to 24 h, while that of the optimized ISG formulation was calculated separately for the studied two drug release phases, namely; during the initial 24 h (Phase I) and after 24 h until 34 days (phase II).

Dissolution Efficiency and Mean Dissolution Time

The dissolution efficiency (DE) and mean dissolution time (MDT) of the fifteen Box-Behnken ISG formulations and the optimized ISG formulation were calculated using Kinet DS 3.0 software (Free license software Rev. 2010, sourceforge.net). The following equations were employed:

$$DE\ (\%) = \frac{\text{area under the dissolution curve up to a certain time}}{\text{area of the rectangle assuming 100\% dissolution at the same time}} \times 100$$

$$MDT = \left(\sum_{j=1}^{n} \hat{t}_j \Delta Q_1\right) \bigg/ \left(\sum_{j=1}^{n} \Delta Q_j\right)$$

where j is the sample number, n the number of time increments considered, $\hat{t}_j$ is the time at midpoint between $t_j$ and $t_{j-1}$, and $\Delta Q_j$ the additional amount of drug dissolved in the period of time $t_j$ and $t_{j-1}$.

Physicochemical Characterization

Differential scanning calorimetry (DSC): The thermal analysis of pure RSV, PLCL and the optimized formulation was investigated using Shimadzu DSC-TA-50 ESI (Tokyo, Japan). A sample of 2 mg from each component was transferred to aluminum crucibles and heated at a heating rate of 10° C./min under a dynamic nitrogen atmosphere.

Fourier transform infrared (FT-IR) spectrum: Samples used in the DSC analysis, were also studied using a Nicolet Is10 (Thermo Scientific, Inc., Waltham, Mass.). The FT-IR spectra of the studied samples were recorded in the range of 4000-400 $Cm^{-1}$.

X-Ray powder diffraction (XRPD): The diffraction pattern of free RSV was recorded using (D/max 2500; Rigaku, Tokyo, Japan) and compared to that of the freeze-dried drug loaded optimized ISG formulation. The scan speed was set at 0.5 degree/min.

Pharmacodynamics and Biochemical Hypolipidemic Efficacy

The protocol for this work received a prior approval from the animal research ethical committee, Faculty of Pharmacy, King Abdulaziz University, Saudi Arabia. It was performed in accordance with the guidelines that ensure the care and use of laboratory animals conformed to the declaration of Helsinki and to the "Principles of Laboratory Animals Care" (NIH publication #85-23, revised in 1985).

Male Wistar rats of an average weight of 300 g were used. Hyperlipidemia was induced in the studied animals by intraperitoneal injection of Poloxamer 407 dissolved in 0.9% saline in a dose of 0.25 g/kg.[25,33] Animals were divided into three groups (n=6). The first group was subjected to intramuscular injection, into the right Gluteus Maximus muscle, of the optimized ISG formulation (Test group). The second group was intramuscularly administered an ISG formulation containing 45% PLCL (25:75) loaded with free RSV without surfactant and PEG (Positive control group). Group three received marketed oral RSV tablets; ROSAVI® 20 mg tablets, SAJA pharmaceuticals Co. Ltd., (Jeddah, Saudi Arabia), that were crushed, dissolved in 1% carboxy methyl cellulose and administered using gastric tube (Reference group). Formulation of the positive control group was prepared utilizing the same procedure mentioned above during development of the ISG system except that no surfactant or plasticizer were added. The test and positive control groups were compared to study the effect of incorporation of the surfactant and plasticizer on the drug initial burst and the profile of drug release in vivo. A dose of 20 mg/kg was administered to each rat.[34,35] Blood samples were withdrawn at 0.5, 1, 2, 24, 48 h, then after 3, 5, 7, 10, 14, 17 and 21 days. The serum was separated from each blood sample by centrifugation at 10000 rpm for 5 minutes. The collected serum samples were evaluated for total cholesterol and triglycerides using a specified lipid kit (Crescent diagnostics industry, Jeddah, Saudi Arabia).

Statistical Analysis of the Pharmacodynamics Data

The data obtained from the pharmacodynamics study were statistically analyzed at p-value <0.05 using Graph Prism 6 software (San Diego, Calif.). Two-way analysis of variance followed by Tukey's multiple comparison test was used to indicate the difference between the studied groups.

Results and Discussion

Preliminary Study

In this section, the initial RSV release from ISG formulations containing different concentrations of PLCL without surfactant and plasticizer was investigated. The selection of the proper polymer is fundamental to obtain the desired drug release profile from the ISG system. The characteristics of PLCL are dependent on the molecular weight and the ratio of both lactic and caprolactone in the polymer chain. PLCL with a higher poly-caprolactone ratio results in a more hydrophobic polymer.[36] Two PLCL grades (80:20 and 25:75) with different lactide and caprolactone ratios were investigated in this study. PLCL (25:75) and (80:20) were used in a concentration range of 20-40% w/v, in NMP, to prepare six different ISG formulations. A polymeric concentration less than 20% often gives a fast drug release and high initial drug burst as previously stated for ISG systems loaded with Poly lactide-co-glycolide.[4,16,24,37,38] Viscus polymeric solutions of poor syringeability and injectability are often obtained from ISG systems that contain a greater polymer concentration (above 50-60%). 24,25

Table 2 demonstrates the obtained results for the in vitro release of RSV from the prepared six ISG formulations after 0.5, 2 and 24 h. Lower initial drug release was observed from the ISG formulation prepared utilizing PLCL (25:75) and higher polymer concentration. This finding may be attributed to the increase in viscosity of the polymeric drug system when higher polymer concentration and more hydrophobic ISG system was used.[39] Xin et al studied the release of hydrochloric thiothixene from polylactic acid ISG containing different polymeric concentrations and reported higher initial drug release from ISG containing low polymer concentration and attributed this behavior to the polymeric matrix viscosity.[40] Moreover, low initial drug release from PLCL (25:75) ISG formulations may be attributed to the higher molecular weight and lower water uptake of this polymer when compared to PLCL (80:20). Dalmoro et al, reported the same finding for the release of a-tocopherol from ISG systems containing different copolymers of ε-caprolactone and L-lactide and mentioned lower drug release from the more hydrophobic PLCL (10:90) when compared to PLCL containing higher ratios of lactide.[36] The studied ISG formulations exhibited RSV release of 40.24±2.16-60.01±3.01, 46.32±1.87-76.14±2.52 and 59.60±1.20-88.57±0.92% after 0.5, 2 and 24 h, respectively. Accordingly, we have studied the incorporation of different surfactants of different HLB and PEG of different molecular weight to decrease the amount of drug released during the first 24 h and so avoid the expected toxic drug effect.

TABLE 2

Percent of rosuvastatin released from in situ gel formulations containing different concentrations of PLCL (80: 20) and (25: 75) in phosphate buffer of pH 7.4.

| ISG Formulation | | Time | | |
|---|---|---|---|---|
| Polymer | Concentration | 0.5 h | 2 h | 24 h |
| PLCL | 20 | 60.01 ± 3.01 | 76.14 ± 2.52 | 88.57 ± 0.92 |
| (80:20) | 30 | 52.49 ± 2.86 | 69.06 ± 2.54 | 75.92 ± 1.63 |
|  | 40 | 44.22 ± 3.90 | 50.44 ± 3.17 | 64.30 ± 0.40 |
| PLCL | 20 | 55.08 ± 2.04 | 70.24 ± 0.88 | 82.37 ± 1.48 |
| (25:70) | 30 | 48.22 ± 2.37 | 64.16 ± 0.76 | 71.53 ± 0.63 |
|  | 40 | 40.24 ± 2.16 | 46.32 ± 1.87 | 59.60 ± 1.20 |

Plackett-Burman Screening Design

After preparation and investigation of the in vitro release profile of the Placket-Burman ISG formulations, the observed values for $Y_1$, $Y_2$ and $Y_3$ were calculated and the obtained data were tabulated in Table 1.

Figure 1B:
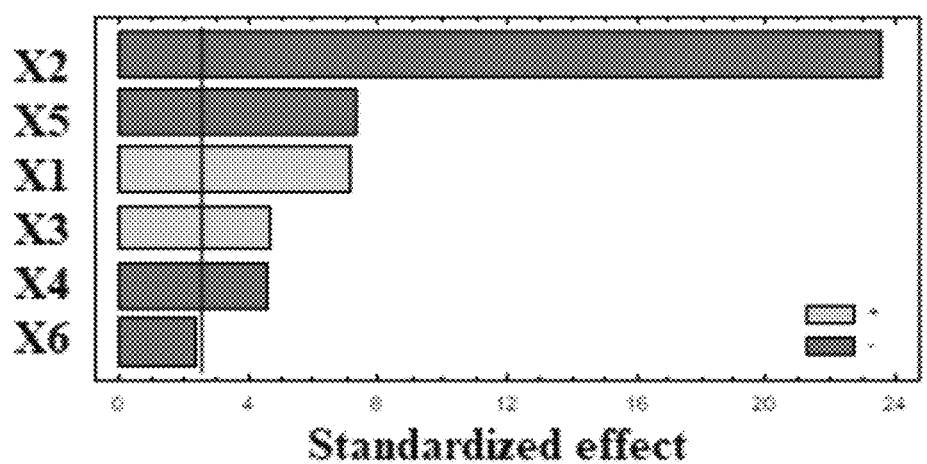
Figure 1C:
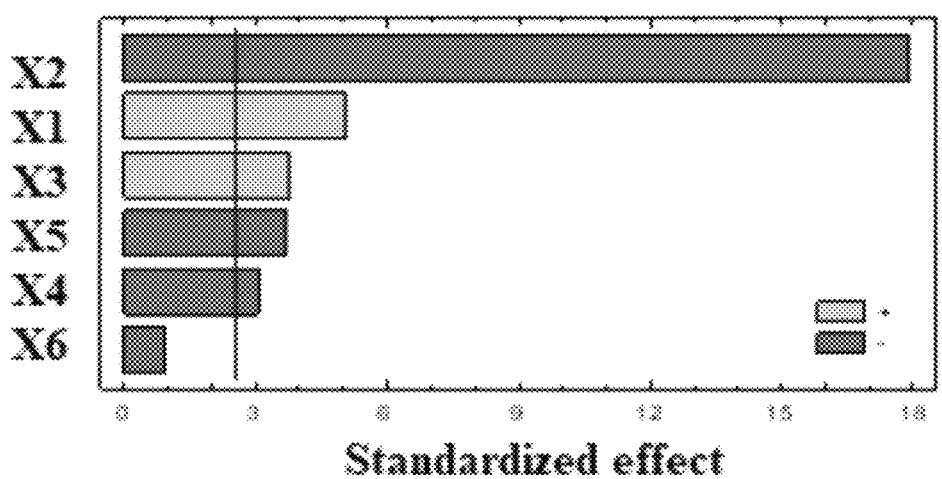
Figure 2A:
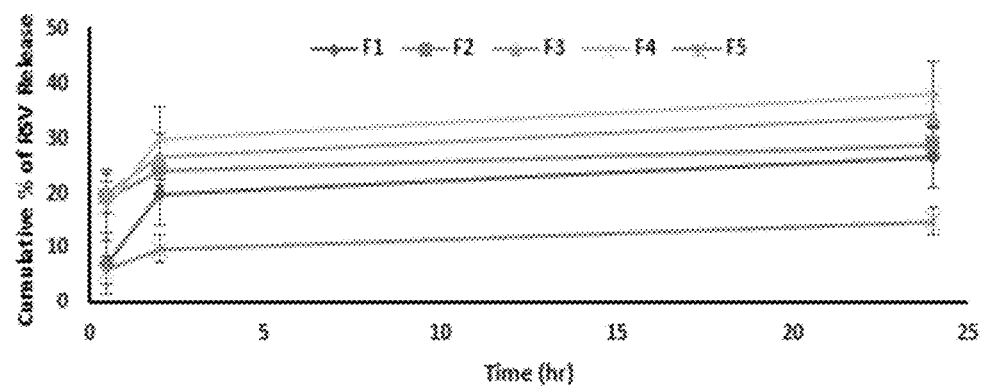
FIG. 2A-D. Percent of rosuvastatin released into phosphate buffer solution of pH 7.4 as a function of time from the Box-Behnken (A, B and C) and the optimized ISG formulation (D).
Figure 2B:
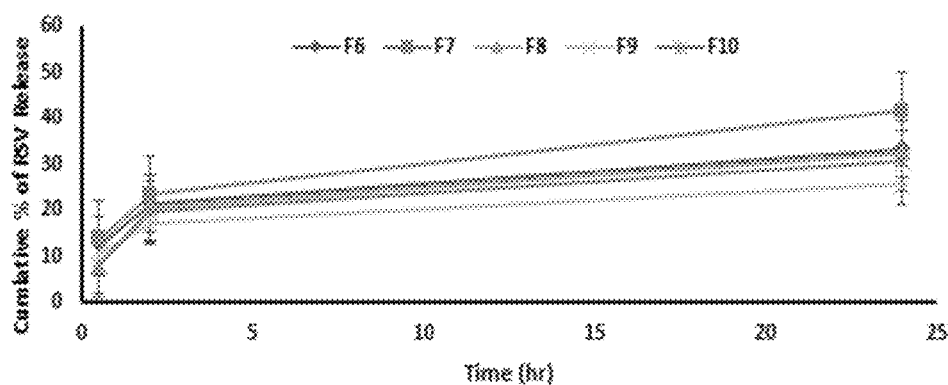
Figure 2C:
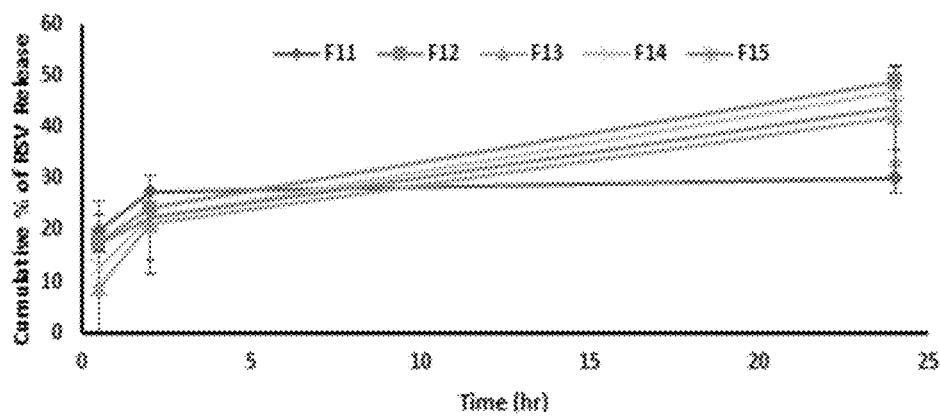
Figure 2D:
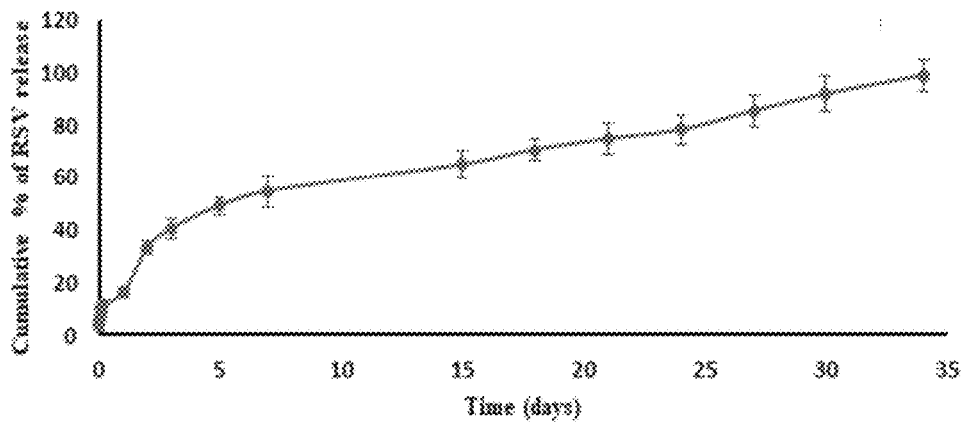
Figure 3:
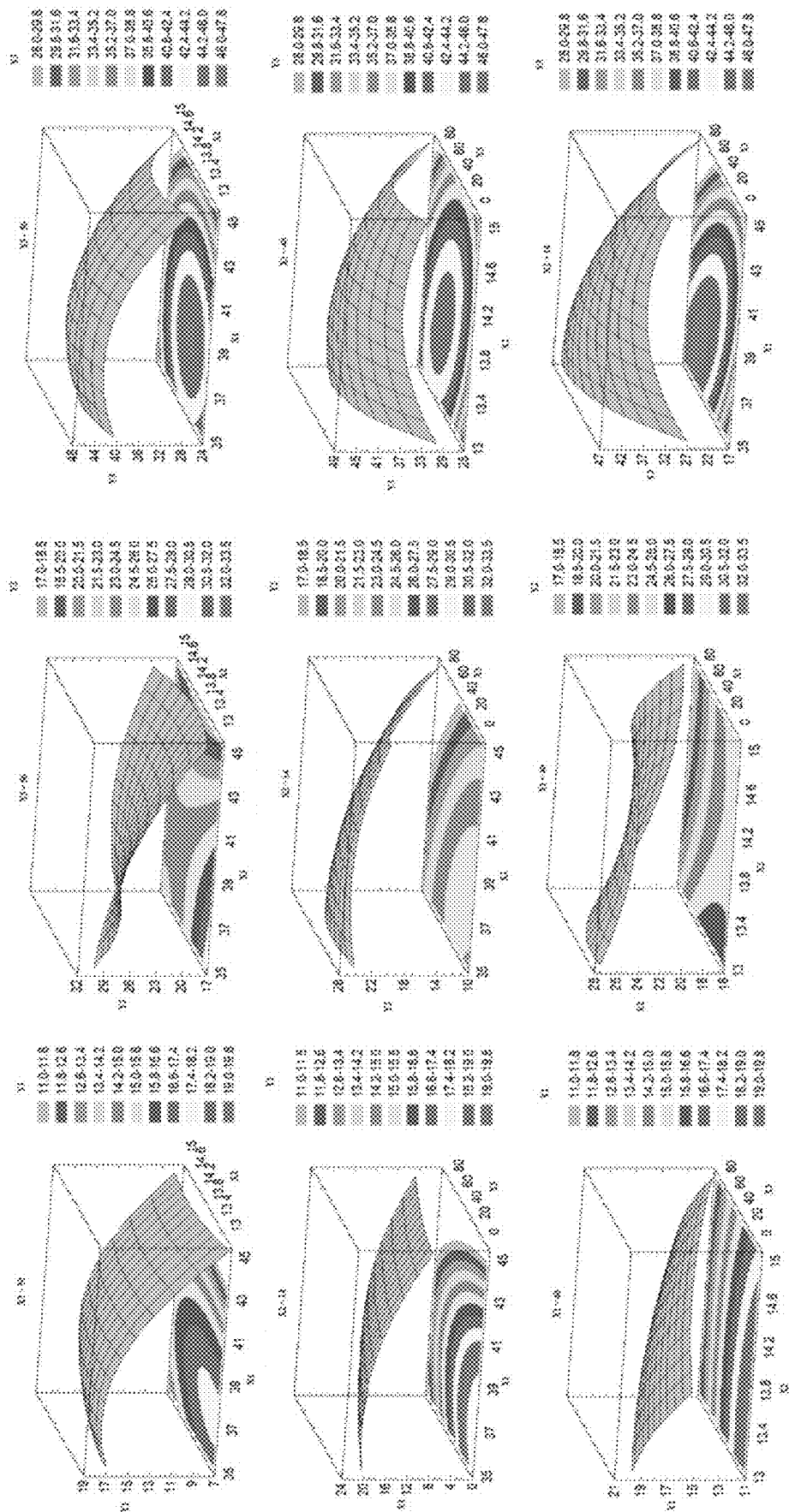
FIG. 3. Estimated response surface plots for the effect of the independent variables on the drug release after 0.5 h ($Y_1$), 2 h ($Y_2$) and 24 h ($Y_3$) from the Box-Behnken ISG formulations.

Analysis of variance (ANOVA) for the effect of the studied variables on $Y_1$ indicated a significant effect of $X_1$, $X_2$ and $X_5$ as graphically illustrated in the Pareto chart (FIG. 1A-C). A reference line at a P-value of 0.05 is observed in this chart. Any factor effect that exceeds this line is significantly affecting the studied response. P-values of 0.0257, 0.0003 and 0.0119, were obtained for $X_1$, $X_2$ and $X_5$, respectively. The obtained R-squared value indicated that the model as fitted explains 95.54% of the variability on the release after 0.5 h, while the adjusted R-squared value, which is more suitable for comparing models with different numbers of independent variables, was 90.18%. The model indicated that to obtain a minimum value for $Y_1$ of 8.54%, the independent variables $X_1$, $X_2$ and $X_5$ should be 25:75, 40% and 14.75, respectively. After analyzing the independent variables by multiple regressions, the obtained polynomial equation of the fitted model for the release after 0.5 h, was found to be: $Y_1=101.745+0.266*X_1-2.024*X_2+0.0027*X_3-0.748*X_4-1.681*X_5-0.656*X_6$ The effect of polymer concentration ($X_1$) and poly lactic: poly caprolactone ratio ($X_2$) has been discussed in the preliminary study section. The concept of incorporation of surfactant during development of ISG system has not gained much attention in the literature. Poly (ethylene oxide)/poly (propylene oxide)/poly (ethylene oxide) triblock copolymers (pluronic) has been added to poly lactic-co-glycolic acid (PLGA) and poly D, L-lactide based ISG systems for delivery of Hen egg protein and Fluorescein (low molecular weight model drug molecule), respectively.[41,42] Also SPAN® (sorbitan monopalmitate) 20, SPAN® (sorbitan monopalmitate) 80, TWEEN® (polysorbate) 20, TWEEN® (polysorbate) 60, CHREMOPHORE® EL (PEG-35 castor oil), and CHREMOPHORE® RH 40 (PEG-40 castor oil) have been added to different PLGA in situ implant system loaded with tamsulosin. Authors mentioned that the incorporated surfactants successfully lowered the in vitro release rate of tamsulosin from the prepared formulations.[43] They attributed this behavior to the formation of a phase boundary between the polymeric matrix and the surrounding aqueous phase. The surfactant hydrophobic part is directed toward the hydrophobic polymer matrix while the hydrophilic part of the surfactant is extended in the aqueous phase. In our work, we have explored the effect of surfactant HLB and surfactant concentration, and found that the former ($X_5$) had a marked significant effect on $Y_1$. Formation of a phase boundary at higher surfactant HLB value was found to have a significant effect on the drug release, the effect which could be attributed to establishment of a well-developed barrier between the polymeric matrix and the external aqueous phase when using more hydrophilic surfactant.

Statistical analysis for the effect of the studied factors on $Y_2$ showed the significant effect of $X_1$, $X_2$, $X_3$, $X_4$, and $X_5$ at P-values of 0.0009, 0.00008, 0.0053, 0.0059 and 0.0007, respectively. The Pareto chart, FIG. 1A-C, confirmed this finding. The obtained values for R-Squared and adjusted R-squared were 99.2963% and 98.4518%, respectively. The polynomial equation of the fitted model for the release after 2 h, after analyzing the independent variables by multiple regressions, was found to be: $Y_2=117.387+0.238*X_1-2.176*X_2+0.002*X_3-0.850*X_4-1.273*X_5-1.116*X_6$ It is noteworthy to mention that the significant factors affecting $Y_2$ was comparative to that obtained for $Y_1$. Both were affected by $X_1$, $X_2$ and $X_5$, but $Y_2$ was also affected by $X_3$ and $X_4$. These results indicate that the molecular weight and the concentration of PEG showed a marked significant effect on $Y_2$. In this study, PEG was added due to its plasticizing action and solubilizing power. Plasticizer is a substance which is added to decrease the attraction force between polymer chains and so make them more flexible. It has been previously mentioned that PEG affects the initial drug release from ISG system possibly by its solubilizing power that permits uniform distribution of the drug particles inside the polymeric matrix and decreases adsorption of any drug particles at the surface. This effect was recently mentioned by Ibrahim et al who studied the effect of incorporation of PEG on the initial release of meloxicam from PLGA based ISG system.[38] Tarek et al, recently stated that the release of atorvastatin from PLGA ISG system was significantly affected by the addition of PEG.[24] They attributed this behavior to the plasticizing action of PEG which decreased the polymer glass transition temperature and so, facilitated congealing of the polymer.

Moreover, the obtained results for RSV release from the prepared ISG formulations after 24 h was markedly affected by the same factors affecting the drug release after 2 h. ANOVA demonstrated that $X_1$, $X_2$, $X_3$, $X_4$ and $X_5$ were significantly affecting $Y_3$ at P-values of 0.039, 0.0002, 0.0128, 0.0288 and 0.0143, respectively as graphically illustrated in the pareto chart of FIG. 1A-C. The R-Squared statistic indicates that the model as fitted explains 98.7134% of the variability. The adjusted R-squared value was found to be 97.1695%. The following polynomial equation that describes the effect of variables on $Y_3$ was obtained: $Y_3=131.599+0.253*X_1-2.453*X_2+0.003*X_3-0.833*X_4-0.942*X_5-0.624*X_6$ Data obtained from the screening study denoted that, PLCL concentration, poly lactic: poly caprolactone ratio and surfactant HLB had a pronounced effect on the drug release after 0.5 h while, the same factors in addition to PEG molecular weight and PEG concentration had a significant effect on the drug release after 2 and 24 h. So, it could be concluded that, PLCL concentration that affects the polymeric matrix density and viscosity, hydrophobicity of the polymer and surfactant concentration promote the process of in situ gelling formation by solvent exchange mechanism during the first 24 h possibly by decreasing the number and size of pores in the matrix that occurs during the solvent exchange process. In addition, the formation of a phase boundary between the polymeric matrix and the surrounding aqueous phase brought about by the incorporation of surfactant also decreased the drug release. This boundary phase is more efficient at higher surfactant HLB and is not affected by the surfactant concentration. Finally, addition of PEG decreased the drug release from the ISG system after 2 h and 24 h. This effect was noticeable with low molecular weight PEG that is liquid or low-melting solid, which makes the polymeric matrix more flexible (plasticizing action) and promotes uniform drug distribution inside the polymeric matrix yet, this effect was not effective during the first 0.5 h of the drug release.

Among the design points, maximum desirability was achieved at run 6. To prepare an ISG formulation characterized by minimum drug release after 0.5 h, 2 h and 24 h, factors $X_1$-$X_5$ need to be optimized to achieve the optimum level of hydrophobic PLCL (25:75), the optimum level of low molecular weight PEG at high surfactant HLB. These factors were subsequently optimized, using the Box-Behnken design, at three levels of PLCL 25:75 concentrations, three levels of high surfactant HLB values and three levels of surfactant to PEG 400 ratios. A fixed concentration of PEG-Surfactant mixture (10% w/v based on the total formulation) at varied ratios was added to study the effect of presence, absence and a combination of both components.

Box-Behnken Optimization Design

Based on the screening study, three formulation factors were optimized for their effect on RSV release from the proposed ISG Box-Behnken formulations. These formulations were characterized for the in vitro drug release after 0.5 h ($Y_1$), 2 h ($Y_2$) and 24 h ($Y_3$) as described earlier. The in vitro release profiles of these formulations are demonstrated graphically in FIG. 2A-D. The observed and predicted values for RSV release at the specified time points are listed in Table 3.

TABLE 3

Compositions of rosuvastatin in situ gel formulations generated by the Box-Behnken design, and the observed and predicted values of $Y_1$-$Y_3$.

| | $X_1'$ | $X_2'$ | $X_3'$ | $Y_1$ (%) | | $Y_2$ (%) | | $Y_3$ (%) | |
|---|---|---|---|---|---|---|---|---|---|
| Formulation | (%) | (HLB) | (Ratio) | Observed | Predicted | Observed | Predicted | Observed | Predicted |
| ISG 1 | 45 | 15 | 50:50 | 7.29 ± 4.11 | 7.90 | 19.84 ± 2.54 | 19.77 | 26.77 ± 0.94 | 24.44 |
| ISG 2 | 35 | 14 | 20:80 | 19.17 ± 3.82 | 20.22 | 24.11 ± 1.19 | 24.04 | 28.87 ± 1.58 | 26.70 |
| ISG 3 | 40 | 15 | 20:80 | 20.28 ± 4.26 | 17.75 | 26.56 ± 3.97 | 25.72 | 34.01 ± 1.53 | 34.87 |
| ISG 4 | 35 | 13 | 50:50 | 17.52 ± 3.01 | 16.91 | 29.94 ± 2.63 | 30.01 | 37.93 ± 1.73 | 40.26 |
| ISG 5 | 45 | 14 | 80:20 | 6.07 ± 4.71 | 5.02 | 9.96 ± 3.04 | 10.04 | 14.97 ± 2.63 | 17.14 |
| ISG 6 | 35 | 15 | 50:50 | 12.51 ± 2.68 | 13.99 | 21.46 ± 2.06 | 22.37 | 33.37 ± 1.80 | 34.67 |
| ISG 7 | 40 | 14 | 50:50 | 13.93 ± 3.27 | 16.36 | 23.44 ± 1.83 | 23.34 | 41.76 ± 1.85 | 44.89 |
| ISG 8 | 45 | 14 | 20:80 | 8.2 ± 2.91 | 10.12 | 20.64 ± 1.11 | 21.55 | 32.48 ± 1.47 | 33.95 |
| ISG 9 | 40 | 15 | 80:20 | 10.85 ± 3.84 | 11.28 | 17.05 ± 2.26 | 17.05 | 25.58 ± 1.72 | 25.75 |
| ISG 10 | 45 | 13 | 50:50 | 8.56 ± 3.33 | 7.08 | 19.7 ± 2.13 | 18.79 | 30.72 ± 1.17 | 29.42 |
| ISG 11 | 40 | 13 | 20:80 | 20.00 ± 1.87 | 19.56 | 27.46 ± 1.27 | 27.46 | 30.22 ± 1.49 | 30.05 |
| ISG 12 | 40 | 14 | 50:50 | 17.77 ± 1.86 | 16.36 | 24.22 ± 1.02 | 23.34 | 48.97 ± 1.40 | 44.89 |
| ISG 13 | 40 | 13 | 80:20 | 9.03 ± 2.73 | 11.56 | 21.13 ± 1.39 | 21.97 | 42.0 ± 1.53 | 41.14 |
| ISG 14 | 35 | 14 | 80:20 | 12.76 ± 3.37 | 10.84 | 22.28 ± 2.91 | 21.37 | 46.94 ± 1.84 | 45.47 |
| ISG 15 | 40 | 14 | 50:50 | 17.39 ± 1.02 | 16.36 | 22.35 ± 1.75 | 23.34 | 43.94 ± 1.22 | 44.89 |

Abbreviations: $X_1'$, poly lactic acid-co-ε-caprolactone concentration; $X_2$, Surfactant HLB; $X_3'$, Surfactant: PEG 400 ratio; $Y_1$, drug release after 0.5 h; $Y_2$, drug release after 2 h; $Y_3$, drug release after 24 h.

The in vitro release of RSV from the prepared Box-Behnken ISG formulations after 0.5, 2 and 24 h was in the range of 6.07±4.71-20.28±4.26, 9.96±3.04-29.94±2.63 and 14.97±2.63-48.97±1.40, respectively. These results are considerably lower than their corresponding ISG formulations used in the preliminary study and in the Plackett-Burman screening design.

Effect of the independent variables on $Y_1$-$Y_3$

Results of RSV in vitro release were statistically analyzed and the obtained results for the estimated effects, F-ratios and P-values are demonstrated in Table 4. Accordingly; $X_1'$, $X_3'$ and $X_1'X_1'$ were significantly affecting $Y_1$ while, $X_1'$, $X_2'$, $X_3'$, $X_1'X_1'$, $X_1'X_2'$, $X_1'X_3'$, $X_2'X_2'$ and $X_3'X_3'$ had a marked significant effect on $Y_2$. Also, $X_1'$, $X_1'X_1'$, $X_1'X_3'$, $X_2'X_2'$, $X_2'X_3'$ and $X_3'X_3'$ were significantly affecting $Y_3$. When the estimated effect has a positive sign value, this is an indication of a synergistic effect of this factor on the selected response, while an antagonistic effect is expected when a negative sign is obtained. The F-ratio is used to compare between the actual and the expected variation of variable averages; an F-ratio that is greater than 1 is an indication of a location effect, and hence, the P-value is used to notify the significant level. A factor is considered significant if the P-value differs from 0 and is less than 0.05. Three-dimensional response surface plots were constructed to explain the effect of changing two independent variables, when the third variable was kept at its intermediate level, on a studied response. These plots are graphically illustrated in FIG. 3. The polynomial equations that relate the studied factors and drug release after 0.5, 2 and 24 h were found to be:

$$Y_1=-228.609+9.785*X_1'+11.259*X_2'-0.326*X_3'-0.168*X_1'^2+0.187*X_1'X_2'+0.004*X_1'X_3'-0.702*X_2'^2+0.008*X_2'X_3'-0.0002*X_3'^2$$

$$Y_2=461.232+0.764*X_1'-62.921*X_2'+0.581*X_3'-0.088*X_1'^2+0.431*X_1'X_2'-0.009*X_1'X_3'+1.601*X_2'^2-0.016*X_2'X_3'-0.0007*X_3'^2$$

$$Y_3=-1516.860+24.026*X_1'+148.960*X_2'+3.114*X_3'-0.297*X_1'^2+0.031*X_1'X_2'-0.036*X_1'X_3'-5.278*X_2'^2-0.101*X_2'X_3'-0.003*X_3'^2$$

TABLE 4

Estimated effects of factors, F-ratio, and P-values for rosuvastatin release after 0.5 h ($Y_1$), 2 h ($Y_2$), 24 h ($Y_3$) from the Box-Behnken ISG formulations.

| | $Y_1$ | | | $Y_2$ | | | $Y_3$ | | |
|---|---|---|---|---|---|---|---|---|---|
| Factors | Estimated effect | F-ratio | P-value | Estimated effect | F-ratio | P-value | Estimated effect | F-ratio | P-value |
| $X_1'$ | 7.96 | 17.20 | 0.0089* | −6.9125 | 73.60 | 0.0004* | −10.5425 | 19.53 | 0.0069* |
| $X_2'$ | −1.045 | 0.30 | 0.6095 | −3.33 | 17.08 | 0.0091* | −5.285 | 4.91 | 0.0776 |
| $X_3'$ | −7.235 | 14.21 | 0.0130* | −7.0875 | 77.37 | 0.0003* | 0.9775 | 0.17 | 0.6989 |
| $X_1'X_1'$ | −8.38333 | 8.81 | 0.0312* | −4.40417 | 13.79 | 0.0138* | −14.83 | 17.84 | 0.0083* |
| $X_1'X_2'$ | 1.87 | 0.47 | 0.5215 | 4.31 | 14.31 | 0.0129* | 0.305 | 0.01 | 0.9315 |
| $X_1'X_3'$ | 2.14 | 0.62 | 0.4661 | −4.425 | 15.08 | 0.0116* | −17.79 | 27.81 | 0.0033* |
| $X_2'X_2'$ | −1.40333 | 0.25 | 0.6404 | 3.20083 | 7.28 | 0.0428* | −10.555 | 9.04 | 0.0299* |
| $X_2'X_3'$ | 0.77 | 0.08 | 0.7880 | −1.59 | 1.95 | 0.2217 | −10.105 | 8.97 | 0.0303* |
| $X_3'X_3'$ | −1.24333 | 0.19 | 0.6782 | −3.77417 | 10.13 | 0.0245* | −13.32 | 14.39 | 0.0127* |

Note: * Indicates significant effect of this factor on the studied response.

Abbreviations: $X_1'$, Poly(lactide-co-ε-caprolactone) 25:75 concentrations; $X_2$, surfactant HLB; $X_3'$, surfactant: polyethylene glycol 400 ratio; $X_1'X_1'$, $X_3'X_3'$ are the quadratic terms for the factors; $X_1'X_2'$, $X_1'X_3'$, $X_2'X_3'$ are the interaction terms between factors.

Based on the above finding, PLCL (25:75) concentration ($X_1$) had a significant antagonistic effect on the drug release at all the studied time points ($Y_1$-$Y_3$). This effect may be attributed to the increase in the polymeric drug ISG system viscosity, as described earlier. The surfactant HLB ($X_2'$) only affected the drug release after 2 h ($Y_2$), which could be attributed to the establishment of an efficient boundary phase by the surfactant molecules at the outer layer of the hydrophobic polymeric matrix after 2 h of ISG injection in the buffer medium. The drug release from this system at 0.5 h and 24 h was not affected by $X_2$ possibly due to partial localization of the surfactant molecules at the boundary and so incomplete formation of the boundary phase (effect on $Y_1$) while, the interaction effect of this factor ($X_2X_2$) markedly affected $Y_3$. Similarly, surfactant: PEG 400 ratio ($X_3'$) affected RSV release in the same way but with a different mechanism, as explained in the above sections.

To prepare an optimized ISG formulation characterized by RSV release of 5.17, 10.05 and 14.97% after 0.5 h, 2 h and 24 h, respectively, the optimum levels of $X_1'$, $X_2'$ and $X_3'$ should be 45%, 14.25 and 80:20, respectively.

Characterization of the Optimized RSV ISG Formulation

The in vitro release of RSV from the optimized ISG formulation is illustrated in FIG. 2D. During the first 24 h, an initial fast release phase was observed that was followed by a second controlled (slow) release phase that lasts for days. In the first phase, a high initial drug release is expected from this system since the ISG formulation is administered as a liquid. Accordingly, a lag time is present between injection of the liquid and development of a semi-solid gel by solvent exchange mechanism. We tried to decrease the drug release during this period and successfully achieved observed values of 5.51±2.34, 10.48±2.01 and 16.26±1.94% for $Y_1$, $Y_2$ and $Y_3$, respectively. The predicted values for the same responses were 5.17, 10.05 and 14.96%, respectively. In the second phase, a diffusion-controlled slower drug release from the semi-solid polymeric drug matrix was observed. It has been previously mentioned that the drug release from ISG systems is mostly triphasic but biphasic release was also reported.[37] In the present study, the second phase lasts for about 34 days. Therefore, the screening and the optimization techniques have been successfully implemented to develop RSV ISG system with minimum initial drug burst that controls the drug release for 34 days. The prepared optimized formulation was clear, of slightly white color and neutral pH (7.43). Acceptable syringeability (39.98±3.12 N) and flow rate (0.134 mL/Second) were obtained. Kurakula and Ahmed, reported syringeability values in the range of 37.8±2.3-44.8±2.4 for atorvastatin PLGA based ISG formulations.[25] They reported good syringeability of the system within this range.

Kinetic Treatment of the In Vitro Release Data

According to the $R^2$ values presented in table 5, kinetic analysis of the in vitro release data of the Box-Behnken formulations and the release of RSV from the optimized formulation during the first 24 h (First Phase) were found to follow the Weibull model. Pharmaceutical systems complied with this model demonstrate a linear plot when the logarithm of the amount of drug released is plotted versus the logarithm of time.[44] The computed β values for these formulations were greater than 1, indicating a sigmoid curve of complex release mechanism.[45] This finding is in a good agreement with our interpretation for the reason of the drug initial burst from this system. The drug release from the optimized formulation after the first 24 h and up to 34 days (Second Phase) were found to obey zero-order model with a 13 value of 0.9779 indicating Fickian diffusion with contribution of another release mechanism.

The β value was used to identify the release mechanism since there is a linear relationship between this value and the n exponent used in Peppas model.[45] Unlike the n exponent which is valid only for the first 60% of release, this value can be successfully applied to almost all kinds of dissolution/release curves.[44] As illustrated in table 5, the calculated values indicated a linear relationship between the 13 and the n exponent used in Peppas model to determine the drug release mechanism. This finding was also mentioned by Papadopoulou et al, during their discussion of the use of Weibull function for the discernment of the possible mechanism of drug release.[45]

TABLE 5

In vitro release kinetics, dissolution efficiency and mean dissolution time of rosuvastatin from the Box-Behneken and the optimized formulations.

| Formulation | Zero Order | First Order | Weibull | Hixson-Crowell | Higuchi | N | Baker-Lonsdale | β-value | DE (%) | MDT (h) |
|---|---|---|---|---|---|---|---|---|---|---|
| ISG 1 | 0.546457 | 0.174839 | 0.991191 | 0.331392 | −2.077116 | 1.044 | 0.729411 | 1.049 | 22.973 | 3.403 |
| ISG 2 | 0.362547 | 0.160961 | 0.985495 | 0.221981 | −3.242480 | 1.053 | 0.556405 | 1.059 | 26.578 | 1.904 |
| ISG 3 | 0.435586 | 0.163482 | 0.986613 | 0.246805 | −3.059841 | 1.058 | 0.668237 | 1.065 | 30.788 | 2.273 |
| ISG 4 | 0.481398 | 0.166775 | 0.988366 | 0.274557 | −2.715996 | 1.061 | 0.691206 | 1.069 | 33.768 | 2.633 |
| ISG 5 | 0.589863 | 0.171204 | 0.989115 | 0.313893 | −2.301051 | 1.024 | 0.816771 | 1.024 | 12.600 | 3.798 |
| ISG 6 | 0.592854 | 0.172156 | 0.990139 | 0.325084 | −2.298625 | 1.053 | 0.800842 | 1.059 | 28.654 | 3.391 |
| ISG 7 | 0.679958 | 0.175308 | 0.991133 | 0.360404 | −2.122025 | 1.059 | 0.906112 | 1.067 | 33.765 | 4.594 |
| ISG 8 | 0.636928 | 0.178265 | 0.992242 | 0.369427 | −1.923462 | 1.050 | 0.828876 | 1.056 | 27.331 | 3.804 |
| ISG 9 | 0.5.6206 | 0.170046 | 0.989105 | 0.305403 | −2.434482 | 1.044 | 0.775859 | 1.048 | 22.111 | 3.253 |
| ISG 10 | 0.629013 | 0.176377 | 0.991541 | 0.355936 | −2.027176 | 1.048 | 0.841730 | 1.054 | 25.420 | 4.140 |
| ISG 11 | 0.324519 | 0.160048 | 0.985333 | 0.212286 | −3.267929 | 1.055 | 0.468951 | 1.062 | 28.347 | 1.486 |
| ISG 12 | 0.696881 | 0.175579 | 0.991224 | 0.367404 | −2.099739 | 1.066 | 0.907988 | 1.075 | 39.733 | 4.526 |
| ISG 13 | 0.720206 | 0.182857 | 0.993690 | 0.415801 | −1.718897 | 1.058 | 0.911439 | 1.065 | 33.492 | 4.861 |
| ISG 14 | 0.747802 | 0.180401 | 0.992789 | 0.408531 | −1.817370 | 1.062 | 0.939329 | 1.071 | 36.919 | 5.123 |
| ISG 15 | 0.673134 | 0.174224 | 0.990572 | 0.353776 | −2.179371 | 1.062 | 0.879242 | 1.071 | 36.382 | 4.128 |
| Opt $1^{st}$ phase | 0.570258 | 0.070272 | 0.987033 | 0.243168 | −1.247237 | 1.047 | 0.802972 | 1.049 | 13.547 | 4.004 |
| Opt $2^{nd}$ phase | 0.977922 | 0.9245698 | 0.8724372 | 0.9479236 | 0.8078216 | 0.455 | 0.878368 | 0.347 | 67.131 | 1.084 |

Abbreviations: DE, diffusion coefficient; MDT, mean dissolution time

Dissolution Efficiency and Mean Dissolution Time

Results of the DE for the Box-Behnken formulations and the optimized formulation during the first 24 h (First Phase) were in the range 12.60-36.92%. The MDT for the same formulations were 1.486-5.13 h. The wide range of values obtained for DE and MDT could be attributed to the difference in the composition of the prepared ISG formulations. Ibrahim et al, previously illustrated that the polymer concentration and its intrinsic viscosity had a negative effect on the DE of meloxicam from PLGA/NMP ISG system. They also mentioned that NMP level has a positive effect on the DE from the same system.[38] The DE and MDT for the second release phase of optimized formulation (after 24 h and up to 34 days) were 67.131% and 1.084 h, respectively.

Physicochemical Characterization

Figure 4:
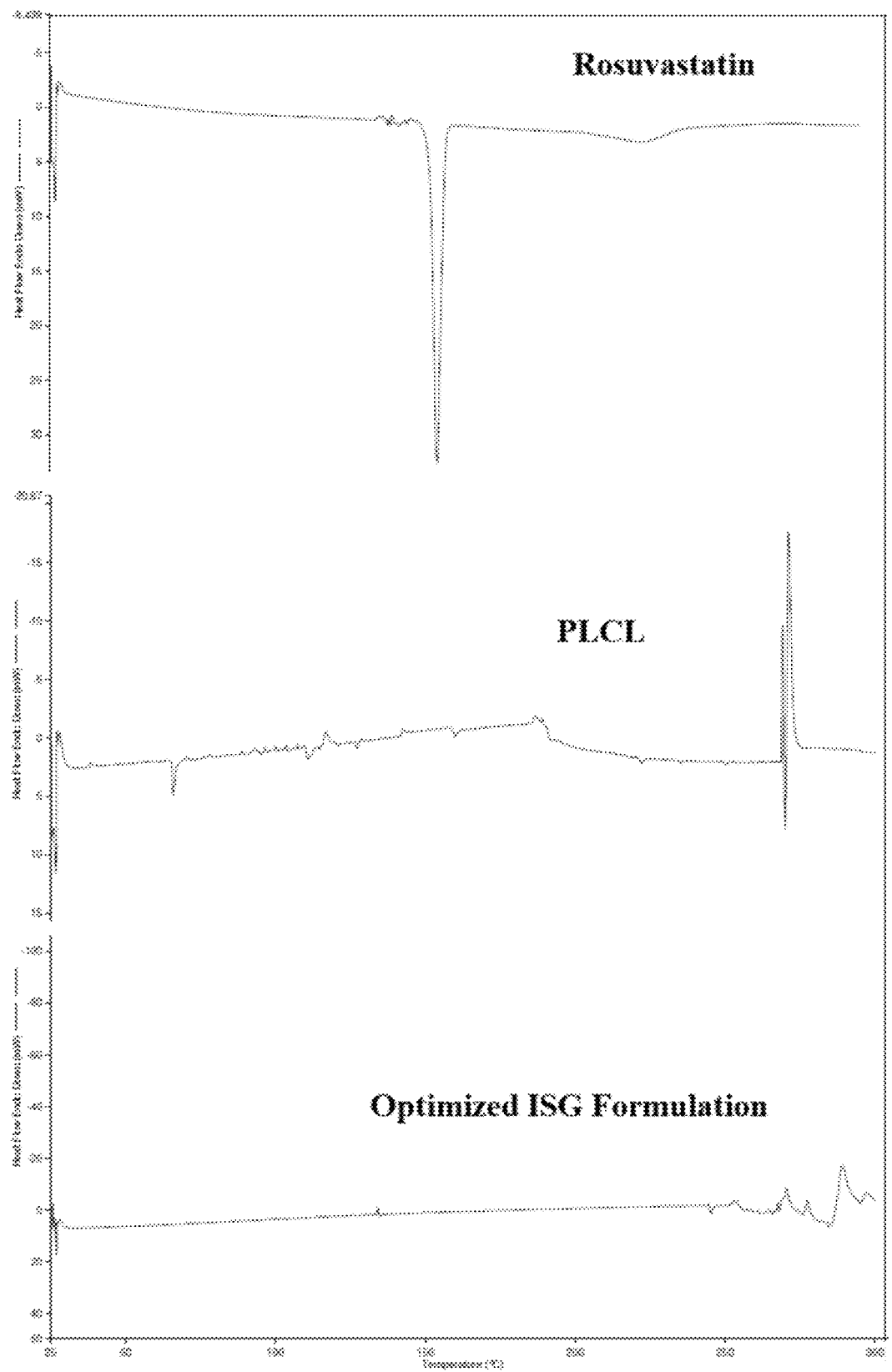
FIG. 4. DSC thermal analysis of pure RSV, PLCL, and the optimized ISG formulation.

The DSC thermogram of RSV (FIG. 4) showed a sharp characteristic endothermic peaks at about 155° C.[46] The thermogram of pure PLCL illustrated a distinguished peak at 70° C. identical to the melting point of polycaprolactone and another peak at about 160° C. corresponding to polylactic acid melting temperatures.[47] A small melting endotherm for polylactic acid was observed due to its relatively low ratio compared to polycaprolactone in the studied polymer (PLCL 25:75). The drug peak was not fully recognized in the DSC thermogram of the optimized drug loaded IS G formulation except for a small peak around 130-140° C. which could be attributed to some change in the drug properties during development of the ISO system. This finding supports complete entrapment and molecular dispersion of RSV in the polymeric matrix. Moreover, the melting points of polycaprolactone and polylactic acid in the optimized ISG formulation seem to be affected by the incorporation of PEG 400 and the studied surfactants.

Figure 5:
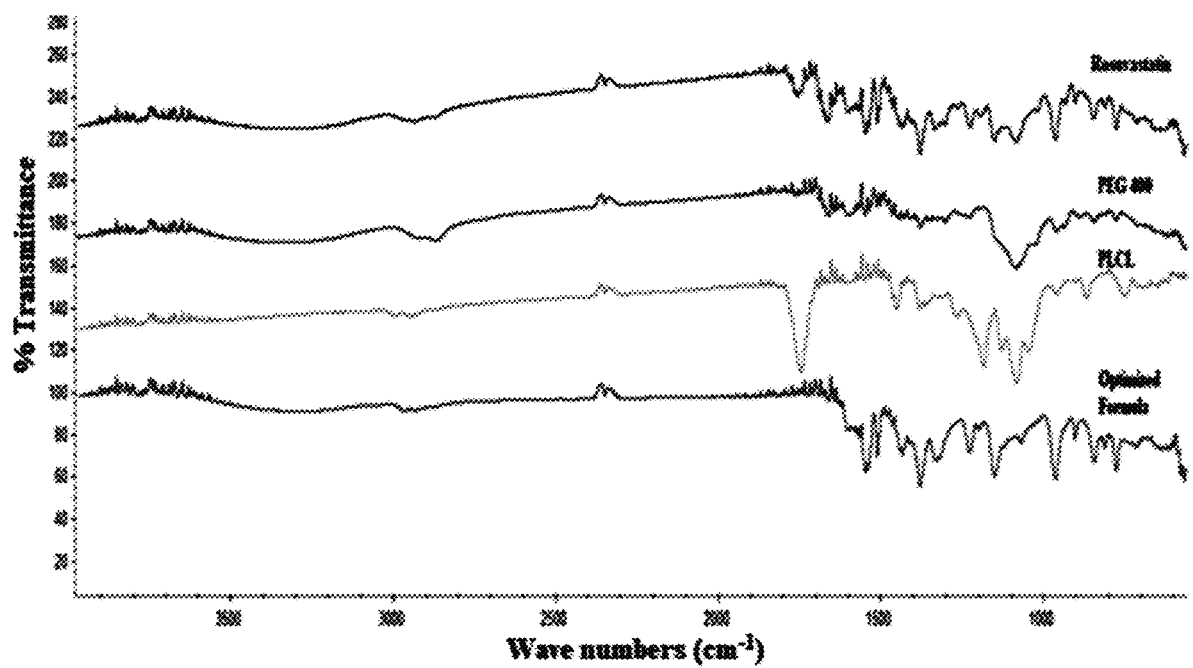
FIG. 5. FT-IR spectroscopy of pure RSV, PEG 400, PLCL and the optimized ISG formulation.

The FT-IR spectrum of RSV (FIG. 5) revealed a broad band for O—H stretching at 3380 cm$^{-1}$, a band at 2920 cm$^{-1}$ for =C—H stretching, a peak at 1550 cm$^{-1}$ for C=C stretching, and a peak at 1515 cm$^{-1}$ for N—H bending. Asymmetric and symmetric bending vibration of $CH_3$ group were detected at 1485 cm$^{-1}$ and 1380 cm$^{-1}$, respectively. The asymmetric vibration of S=O was noticed at 1330 cm$^{-1}$. The bending vibration for C—H and C—F stretching vibrations were detected at 1230 cm$^{-1}$ and 1155 cm$^{-1}$, respectively. The FT-IR spectrum of PEG illustrated a polymer peaks at 1464, 1343 cm$^{-1}$ for C—H bending vibrations. Other PEG peaks at 1279, 1094 cm$^{-1}$ corresponding to O—H and C—O—H stretching. The FT-IR spectrum of PLCL revealed a broad polymer peak at 2919 cm$^{-1}$ corresponding to CH stretching vibration ($CH_2$). Another PLCL peak at 1724 cm$^{-1}$ corresponding to the C=O stretching vibration (Non-conjugated). Also, a characteristic PLCL peak was found at 1164 cm$^{-1}$ corresponding to C—O—C (esters) vibration. The FT-IR spectrum of the optimized drug loaded ISG formulation showed the characteristic drug peaks of S=O and C—F stretching vibration, while other RSV characteristic peaks were overlapped with the PEG and PLCL peaks.

Figures 6A, 6B:
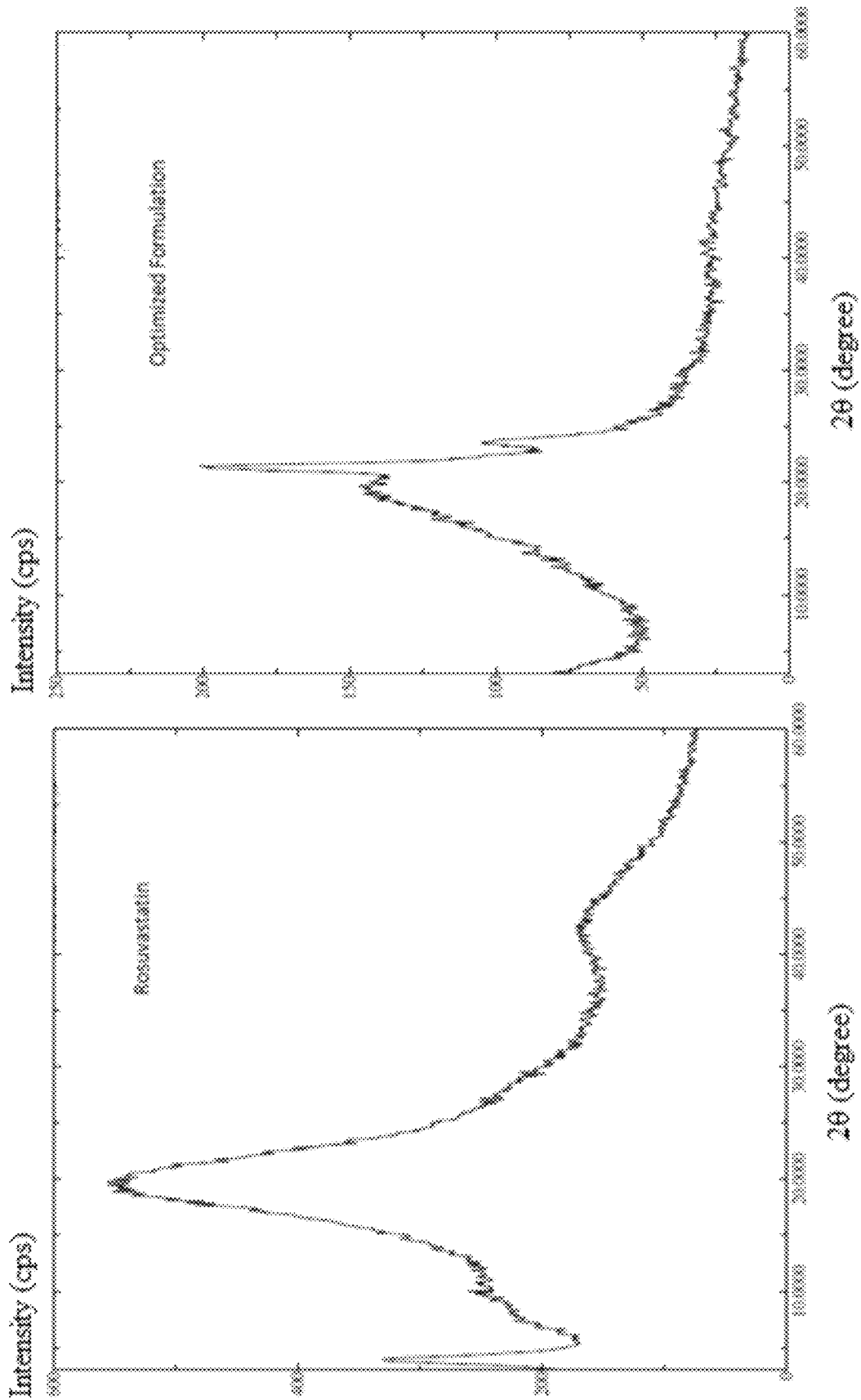
FIG. 6A-B. X-ray diffraction patterns of (A) pure RSV and (B) the optimized ISG formulation.

The X-ray diffraction patterns of pure RSV and the optimized drug loaded ISG formulation are illustrated in FIG. 6A-B. RSV demonstrated broad and numerous distinct diffraction peaks which indicate the crystalline nature of the pure rosuvastatin calcium. The diffraction spectrum of the optimized drug loaded ISG formulation demonstrated halo diffractograms with some changes in the drug characteristic peaks that was confirmed by absence of the drug characteristic peak at 20 diffraction angle of 15.5° and appearance of two sharp peaks at 22° C. and 24° C. This behavior might be attributed to complete dissolving of the pure drug in the PLCL-NMP ISG system with subsequent gelation of the polymeric matrix after injection in the buffer. The above finding indicates that rosuvastatin calcium exhibited slight changes in its crystalline form in the ISG formulation but did not confirm complete transformation into the amorphous form.

Pharmacodynamic and Biochemical Hypolipidemic Efficacy

To investigate the hypolipidemic efficacy of RSV after intramuscular injection of the optimized ISG formulation, the pharmacodynamic and biochemical effects were studied.

Figure 7B:
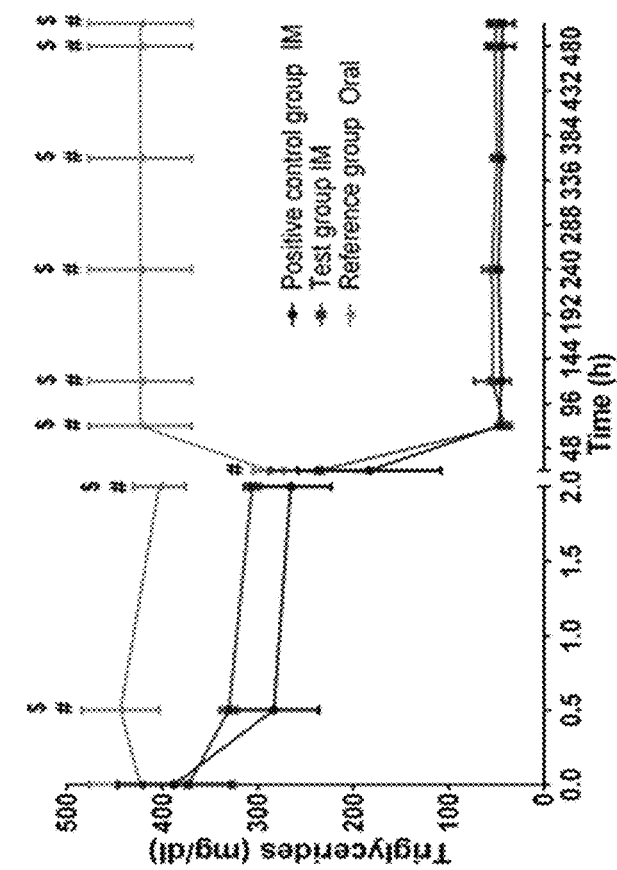
FIG. 7A-B. Total cholesterol level (A) and triglycerides level (B) versus time following administration of RSV in the studied animals. Notes: * Indicates statistical significance between test group and positive control group, S indicates statistical significance between test group and reference group, # indicates statistical significance between positive control group and reference group.
Figure 7A:
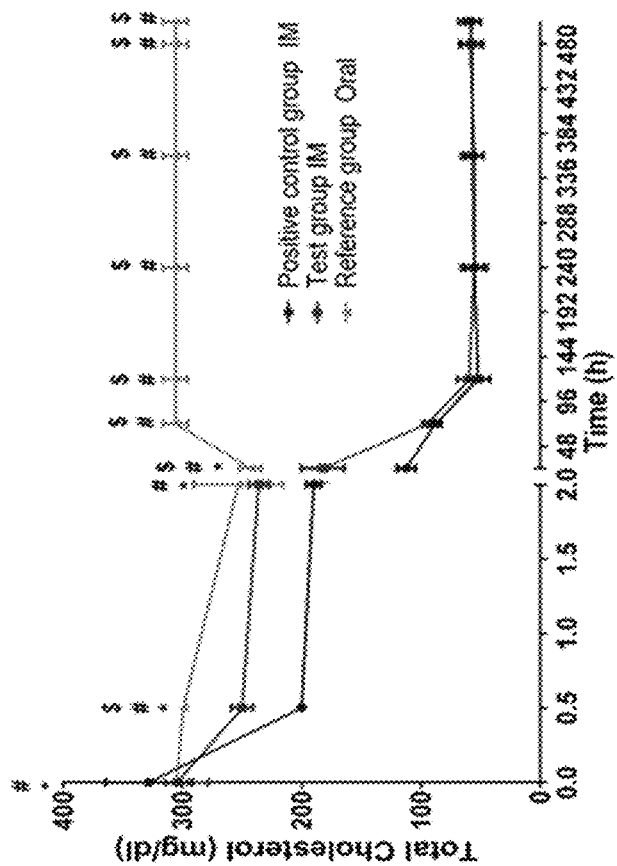

Results obtained were compared to other groups that were given ISG formulation containing 45% PLCL (25:75) loaded with free RSV (positive control) and to oral marketed drug product (reference group). Serum samples were collected from all rats 24 h before induction of hyperlipidemia using Poloxamer 407. Induction of hyperlipidemia was initially confirmed by the change in appearance of the rats' serum from normal clear to milky white. The studied formulations were given to the assigned groups after induction of hyperlipidemia and blood samples were withdrawn from all animals at the predetermined time intervals. The total cholesterol and triglycerides were quantified in the collected samples and data obtained are graphically illustrated in FIG. 7A-B.

Based on the obtained data, high levels of cholesterol and triglycerides were noticed before administration of RSV (time zero). Administration of the ISG formulations and the marketed drug product affected the serum lipid level that was altered by Poloxamer 407. High initial drug release from the ISG formulation loaded with free RSV induced a very low total cholesterol and triglycerides levels in the first 24 h. Similar behavior was noticed from the group treated with the optimized ISG formulation but to a marked lesser extent which is an indication of low initial drug burst from this group. After 24 h of treatment, the group treated with the marketed drug product reduced the total cholesterol and triglycerides by 12.99 and 34.16%, respectively. Groups treated with the ISG formulations showed a sustained reduction in lipid profile that lasted for 21 days. This effect was not observed in the reference group that demonstrated a return to the original high lipid profile after 72 hours of RSV treatment. The effect of the optimized ISG formulation on serum lipids was statistically significant (P<0.05) when compared with ISG loaded with free RSV and the marketed drug product groups.

CONCLUSION

The Plackett-Burman screening and Box-Behnken optimization designs have been successfully implemented to investigate and optimize the significant factors affecting the initial drug burst from PLCL based ISG formulations. An optimized ISG formulation characterized by an initial RSV release of 5.17, 10.05 and 14.97% after 0.5 h, 2 h and 24 h, respectively, was developed. The optimized formulation illustrated acceptable syringeability, good flow rate and was able to extend the in vitro drug release for 34 days. Pharmacodynamic study revealed sustained reduction in the lipid profile that lasts for 21 days with a marked decrease in the serum lipid level from the ISG system loaded with free RSV in the first 24 h.

ACKNOWLEDGMENT

This project was funded by the Deanship of Scientific Research (DSR) at King Abdulaziz University, Jeddah, under grant no. (RG-4-166-38). The inventors, therefore, acknowledge with thanks DSR technical and financial support.

REFERENCES

1. Al-Tahami K, Singh J. Smart polymer based delivery systems for peptides and proteins. *Recent Pat Drug Deliv Formul*. 2007; 1(1):65-71. doi: 10.2174/187221107779814113
2. Huang X, Brazel C S. On the importance and mechanisms of burst release in matrix-controlled drug delivery systems. *J Control Release*. 2001; 73(2-3):121-136.
3. Huang X, Brazel C S. Analysis of burst release of proxyphylline from poly(vinyl alcohol) hydrogels. *Chem Eng Commun*. 2003; 190(4):519-532. doi:10.1080/00986440302081
4. Ahmed T A, Ibrahim H M, Samy A M, Kaseem A, Nutan M T H, Hussain M D. Biodegradable Injectable In Situ Implants and Microparticles for Sustained Release of Montelukast: In Vitro Release, Pharmacokinetics, and Stability. *AAPS PharmSciTech*. 2014; 15(3):772-780. doi:10.1208/s12249-014-0101-3
5. Mallapragada S K, Peppas N A, Colombo P. Crystal dissolution-controlled release systems. II. Metronidazole release from semicrystalline poly(vinyl alcohol) systems. *J Biomed Mater Res*. 1997; 36(1):125-130. http://www.ncbi.nlm.nih.gov/pubmed/9212397. Accessed Jun. 1, 2015.
6. Pekarek K J, Jacob J S, Mathiowitz E. Double-walled polymer microspheres for controlled drug release. *Nature*. 1994; 367(6460):258-260. doi:10.1038/367258a0
7. Pandey S K, Haldar C, Patel D K, Maiti P. Biodegradable Polymers for Potential Delivery Systems for Therapeutics. *Adv Polym Sci*. 2013; 254:169-202. doi:10.1007/12_2012_198
8. Bhise K, Kotwal V, Saifee M, Inamdar N. Biodegradable polymers: Which, when and why? *Indian J Pharm Sci*. 2007; 69(5):616. doi:10.4103/0250-474X.38465
9. Qi F, Wu J, Li H, Ma G. Recent research and development of PLGA/PLA microspheres/nanoparticles: A review in scientific and industrial aspects. *Front Chem Sci Eng*. June 2018:1-14. doi:10.1007/s11705-018-1729-4
10. Daranarong D, Chan R T H, Wanandy N S, Molloy R, Punyodom W, Foster L J R. Electrospun polyhydroxybutyrate and poly(L-lactide-co-ε-caprolactone) composites as nanofibrous scaffolds. *Biomed Res Int*. 2014; 2014:741408. doi:10.1155/2014/741408
11. Jeong S I, Kim S H, Kim Y H, et al. Manufacture of elastic biodegradable PLCL scaffolds for mechano-active vascular tissue engineering. *J Biomater Sci Polym Ed*. 2004; 15(5):645-660.
12. Jung Y, Kim S H, You H J, Kim S-H, Ha Kim Y, Min B G. Application of an elastic biodegradable poly(L-lactide-co-ε-caprolactone) scaffold for cartilage tissue regeneration. *J Biomater Sci Polym Ed*. 2008; 19(8):1073-1085. doi:10.1163/156856208784909336
13. Díaz E, Sandonis I, Valle M B. In Vitro Degradation of Poly(caprolactone)/nHA Composites. *J Nanomater*. 2014; 2014:1-8. doi:10.1155/2014/802435
14. Ibrahim H M, Ahmed T A, Hussain M D, et al. Development of meloxicam in situ implant formulation by quality by design principle. *Drug Dev Ind Pharm*. 2014; 40(1). doi:10.3109/03639045.2012.746360
15. Ahmed T A, Ibrahim H M, Ibrahim F, et al. Development of biodegradable in situ implant and microparticle injectable formulations for sustained delivery of haloperidol. *J Pharm Sci*. 2012; 101(10):3753-3762. doi:10.1002/jps.23250
16. Ahmed T A. Approaches to develop PLGA based in situ gelling system with low initial burst. *Pak J Pharm Sci*. 2015; 28(2):657-665.
17. Gurpreet Singh, Tanurajvir Kaur, Ravinder Kaur A K. Recent biomedical applications and patents on biodegradable polymer-PLGA. *Int J Pharmacol Pharm Sci*. 2014; 1(2):30-42.
18. K KM, Mohanty D, Bakshil D V. An Overview on Design of Experiment in Product Formulation. *Res Rev J Pharm Nanotechnol*. August 2016:61-67.
19. Asadi N, Zilouei H. Optimization of organosolv pretreatment of rice straw for enhanced biohydrogen production using Enterobacter aerogenes. *Bioresour Technol*. 2017; 227:335-344. doi:10.1016/J.BIORTECH.2016.12.073
20. Maged A, Handy S, Shamsuzzaman M, Alsyouf I, Zaied R. Statistical Monitoring and Optimization of Electrochemical Machining using Shewhart Charts and Response Surface Methodology. *Int J Eng Mater Manuf*. 2018; 3(2):68-77. doi:10.26776/ijemm 03.02.2018.01
21. Davies J T, Delfino S F, Feinberg C E, et al. Current and Emerging Uses of Statins in Clinical Therapeutics: A Review. *Lipid Insights*. 2016; 9:13-29. doi:10.4137/LPI.S37450
22. Karasulu H Y, Gundogdu E, Turk U O, et al Enhancing Solubility and Bioavailability of Rosuvastatin into Self Nanoemulsifying Drug Delivery System. *Curr Drug Deliv*. 2018; 15(7):1072-1082. doi:10.2174/1567201815666180226114545
23. Li J, Yang M, Xu W. Development of novel rosuvastatin nanostructured lipid carriers for oral delivery in an animal model. *Drug Des Devel Ther*. 2018; Volume 12:2241-2248. doi:10.2147/DDDT.S169522
24. El-Say K M, Alharby Y, El-Helw A-R, Hosny K M, Ahmed T. Depot injectable atorvastatin biodegradable in situ gel: development, optimization, in vitro, and in vivo evaluation. *Drug Des Devel Ther*. 2016:405. doi:10.2147/DDDT.S98078
25. Kurakula M, Ahmed T A. Co-delivery of atorvastatin nanocrystals in PLGA based in situ gel for anti-hyperlipidemic efficacy. *Curr Drug Deliv*. 2016; 13:1-11.
26. Wagner J G. Interpretation of percent dissolved-time plots derived from in vitro testing of conventional tablets and capsules. *J Pharm Sci*. 1969; 58(10):1253-1257. http://www.ncbi.nlm.nih.gov/pubmed/5349114. Accessed Apr. 26, 2015.
27. Langenbucher F. Linearization of dissolution rate curves by the Weibull distribution. *J Pharm Pharmacol*. 1972; 24(12):979-981. http://www.ncbi.nlm.nih.gov/pubmed/4146531. Accessed Apr. 27, 2019.
28. Hixson A W, Crowell J H. Dependence of Reaction Velocity upon surface and Agitation. *Ind Eng Chem*. 1931; 23(8):923-931. doi:10.1021/ie50260a018
29. Higuchi T. Mechanism of sustained-action medication. Theoretical analysis of rate of release of solid drugs dispersed in solid matrices. *J Pharm Sci*. 1963; 52:1145-1149. http://www.ncbi.nlm.nih.gov/pubmed/14088963. Accessed Apr. 26, 2015.
30. Korsmeyer R W, Gurny R, Doelker E, Buri P, Peppas N A. Mechanisms of solute release from porous hydrophilic polymers. *Int J Pharm*. 1983; 15(1):25-35. doi:10.1016/0378-5173(83)90064-9

31. Peppas N A. Analysis of Fickian and non-Fickian drug release from polymers. *Pharm Acta Helv.* 1985; 60(4): 110-111. http://www.ncbi.nlm.nih.gov/pubmed/4011621. Accessed Apr. 23, 2015.
32. Baker R W, Lonsdale H S. Controlled release: mechanisms and release. In: Taquary, A. C., Lacey, R. E. (Eds), *Controlled Release of Biological Active Agents.* Plenum Press, New York.; 1974:15-71. https://www.popline.org/node/495093. Accessed Apr. 27, 2019.
33. Chaudhary H R, Brocks D R. The single dose poloxamer 407 model of hyperlipidemia; systemic effects on lipids assessed using pharmacokinetic methods, and its effects on adipokines. *J Pharm Pharm Sci.* 2013; 16(1):65-73.
34. Reisin E, Liao J, Lee B S, et al. *Effect of the HMG-CoA Reductase Inhibitor* Rosuvastatin on Early Chronic Kidney Injury in Obese Zucker Rats Fed With an Atherogenic Diet. *Am J Med Sci.* 2009; 338(4):301-309. doi:10.1097/MAJ.0b013e3181b27195
35. Georgieva-Kotetarova M T, Kostadinova I I. Effect of Atorvastatin and Rosuvastatin on Learning and Memory in Rats with Diazepam-Induced Amnesia. *Folia Med (Plovdiv).* 2013; 55(2):58-65. doi:10.2478/folmed-2013-0018
36. Dalmoro A, Barba A A, Lamberti M, Mazzeo M, Venditto V, Lamberti G. Random 1-lactide/ε-caprolactone copolymers as drug delivery materials. *J Mater Sci.* 2014; 49(17):5986-5996. doi:10.1007/s10853-014-8317-x
37. Ahmed T A, Ibrahim H M, Ibrahim F, et al. Development of Biodegradable In Situ Implant and Microparticle Injectable Formulations for Sustained Delivery of Haloperidol. *J Pharm Sci.* 2012; 101(10):3753-3762. doi:10.1002/jps
38. Ibrahim H M, Ahmed T a, Hussain M D, et al. Development of meloxicam in situ implant formulation by quality by design principle. *Drug Dev Ind Pharm.* 2013; 9045:1-8. doi:10.3109/03639045.2012.746360
39. Tefas L R, Tomuta I, Achim M, Vlase L. Development and optimization of quercetin-loaded PLGA nanoparticles by experimental design. *Clujul Med.* 2015; 88(2):214-223. doi:10.15386/cjmed-418
40. Xin C, Lihong W, Qiuyuan L, Hongzhuo L. Injectable long-term control-released in situ gels of hydrochloric thiothixene for the treatment of schizophrenia: preparation, in vitro and in vivo evaluation. *Int J Pharm.* 2014; 469(1):23-30. doi:10.1016/j.ijpharm.2014.04.044
41. DesNoyer J R, McHugh A J. The effect of Pluronic on the protein release kinetics of an injectable drug delivery system. *J Control Release.* 2003; 86(1):15-24. http://www.ncbi.nlm.nih.gov/pubmed/12490369. Accessed Jun. 30, 2015.
42. Patel R B, Carlson A N, Solorio L, Exner A A. Characterization of formulation parameters affecting low molecular weight drug release from in situ forming drug delivery systems. *J Biomed Mater Res A.* 2010; 94(2): 476-484. doi:10.1002/jbm.a.32724
43. Elias-Al-Mamun M, Khan H A, Dewan I, Jalil R-U. In vitro study on tamsulosin release kinetics from biodegradable PLGA in situ implants. *Pak J Pharm Sci.* 2009; 22(4):360-367. http://www.ncbi.nlm.nih.gov/pubmed/19783512. Accessed Jun. 19, 2015.
44. Sousa Lobo J M, Costa P. Modeling and comparison of dissolution profiles. *Eur J Pharm Sci.* 2001; 13:123-133.
45. Papadopoulou V, Kosmidis K, Vlachou M, Macheras P. On the use of the Weibull function for the discernment of drug release mechanisms. *Int J Pharm.* 2006; 309(1-2): 44-50. doi:10.1016/j.ijpharm.2005.10.044
46. Kapure V J, Pande V V, Deshmukh P K. Dissolution Enhancement of Rosuvastatin Calcium by Liquisolid Compact Technique. *J Pharm.* 2013; 2013:315902. doi: 10.1155/2013/315902
47. Chavalitpanya K, Phattanarudee S. Poly(lactic acid)/polycaprolactone blends compatibilized with block copolymer. *Energy Procedia.* 2013; 34:542-548. doi:10.1016/j.egypro.2013.06.783

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An in situ gel formulation comprising:
poly lactide-co-ε-caprolactone (PLCL), wherein the ratio of lactide to caprolactone in PLCL is 25:75 and wherein the PLCL concentration is 40-45% w/v;
a surfactant with a hydrophilic-lipophilic balance value of 14-15;
a plasticizer;
a statin;
wherein the surfactant is a mixture of sorbitan monopalmitate 40 and polysorbate 80; and
wherein a ratio of the surfactant to the plasticizer is 80:20.

2. The in situ gel formulation of claim 1, wherein the statin is rosuvastatin.

3. The in situ gel formulation of claim 1, wherein the plasticizer is polyethylene glycol (PEG) 400.

* * * * *